US011083851B2

(12) United States Patent
Pedde

(10) Patent No.: US 11,083,851 B2
(45) Date of Patent: Aug. 10, 2021

(54) METHODS, SYSTEMS AND DEVICES FOR ADMINISTERING MEDICATION

(71) Applicant: Ethan Pedde, Glasgow, MT (US)

(72) Inventor: Ethan Pedde, Glasgow, MT (US)

(*) Notice: Subject to any disclaimer, the term of this patent is extended or adjusted under 35 U.S.C. 154(b) by 770 days.

(21) Appl. No.: 15/706,662

(22) Filed: Sep. 15, 2017

(65) Prior Publication Data
US 2018/0078710 A1 Mar. 22, 2018

Related U.S. Application Data
(60) Provisional application No. 62/396,101, filed on Sep. 17, 2016.

(51) Int. Cl.
*A61M 5/315* (2006.01)
*A61M 5/24* (2006.01)
*A61M 5/31* (2006.01)
*A61M 5/50* (2006.01)
*A61M 5/32* (2006.01)
*A61M 5/178* (2006.01)
(Continued)

(52) U.S. Cl.
CPC .......... *A61M 5/31545* (2013.01); *A61J 1/201* (2015.05); *A61J 1/2055* (2015.05); *A61J 1/2096* (2013.01); *A61M 5/002* (2013.01); *A61M 5/1782* (2013.01); *A61M 5/24* (2013.01); *A61M 5/3129* (2013.01); *A61M 5/3148* (2013.01); *A61M 5/31535* (2013.01); *A61M 5/31536* (2013.01); *A61M 5/3213* (2013.01); *A61M 5/502* (2013.01); *A61M 2005/5033* (2013.01); *A61M 2210/04* (2013.01)

(58) Field of Classification Search
CPC ........ A61J 1/201; A61J 1/2096; A61J 1/2055; A61M 5/002; A61M 2005/5033; A61M 5/31501
USPC ................................................. 604/208, 232
See application file for complete search history.

(56) References Cited

U.S. PATENT DOCUMENTS 2,565,081 A   8/1951 Maynes
2,705,008 A   3/1955 Melton
(Continued)

FOREIGN PATENT DOCUMENTS

AU     2006204125 A1 *  7/2006
EP        1421961 A2    5/2004
WO    WO-2004028602 A2 *  4/2004

OTHER PUBLICATIONS

University of Michigan IM dosing instructions (Year: 2008).*
(Continued)

*Primary Examiner* — Amy R Weisberg
(74) *Attorney, Agent, or Firm* — Flaig Law Office, PLLC; Jason E. Flaig

(57) ABSTRACT

Systems, methods and devices for administering medication are disclosed. One or more embodiments of a medication delivery device may include a syringe, a needle, a guiding element, and a volume limiter for limiting the amount of medication that can be drawn from a vial. At least one method for administering medication using a medication delivery device, may include: inserting a vial into a guiding element, drawing back on a plunger, removing the guiding element and the vial from a needle to expose the needle, inserting the needle into a patient, depressing the plunger to inject the medication into the patient, and withdrawing the medication delivery device from the patient.

20 Claims, 19 Drawing Sheets

(51) Int. Cl.
*A61M 5/00* (2006.01)
*A61J 1/20* (2006.01)

(56) References Cited

U.S. PATENT DOCUMENTS

| | | | |
|---|---|---|---|
| 2,875,761 A | 3/1959 | Easton et al. | |
| 4,248,225 A * | 2/1981 | Moore | A61M 5/1782 310/17 |
| 4,518,387 A * | 5/1985 | Murphy | A61M 5/422 604/115 |
| 4,563,178 A * | 1/1986 | Santeramo | A61M 5/1782 141/27 |
| 4,564,054 A | 1/1986 | Gustavsson | |
| 5,088,996 A | 2/1992 | Kopfer et al. | |
| 5,104,380 A | 4/1992 | Holman et al. | |
| 5,279,576 A | 1/1994 | Loo et al. | |
| 5,318,544 A * | 6/1994 | Drypen | A61M 5/3155 604/210 |
| 5,827,262 A * | 10/1998 | Neftel | A61J 1/2096 604/414 |
| 6,497,697 B1 | 12/2002 | Cohn | |
| 6,875,205 B2 | 4/2005 | Leinsing | |
| 6,951,551 B2 * | 10/2005 | Hudon | A61M 5/3216 604/192 |
| 7,497,841 B2 | 3/2009 | Alchas | |
| 7,976,510 B2 | 7/2011 | Janish et al. | |
| 8,070,739 B2 | 12/2011 | Zinger et al. | |
| 8,167,863 B2 | 5/2012 | Yow | |
| 8,287,491 B2 | 10/2012 | Burns et al. | |
| 8,753,325 B2 | 6/2014 | Lev et al. | |
| 9,421,323 B2 | 8/2016 | Cabiri et al. | |
| 2003/0004467 A1 | 1/2003 | Musick et al. | |
| 2005/0273054 A1 | 12/2005 | Asch | |
| 2006/0155257 A1 * | 7/2006 | Reynolds | A61J 1/2096 604/414 |
| 2006/0195063 A1 * | 8/2006 | Lim | A61M 5/508 604/110 |
| 2011/0313397 A1 | 12/2011 | Gold | |
| 2013/0150803 A1 | 6/2013 | Shetty et al. | |
| 2015/0080809 A1 | 3/2015 | Dasbach et al. | |
| 2017/0014579 A1 * | 1/2017 | Derby | A61M 5/1782 |

OTHER PUBLICATIONS

Guinea Pig Cages, Oral Ivermectin . . . https://www.guineapigcages.com/forum/threads/22151-Oral-Ivermectin-Dosing-Step-by-Step-with-pics, see exhibit cover sheet for details.
drugs.com, Stelara Dosage, https://www.drugs.com/dosage/stelara.html, accessed Apr. 4, 2017, see exhibit cover sheet for details.
Zoetis, Sileo, https://www.zoetisus.com/products/dogs/sileo/administration.aspx, accessed Apr. 4, 2017, see exhibit cover sheet for details.
Hadleigh Health Technologies, Doseright Syringe Clips, http://hadleighhealthtechnologies.com/doseright/, accessed Apr. 4, 2017, see exhibit cover sheet for details.
Diabetes Forecast, Product Guide . . . , http://www.diabetesforecast.org/2016/mar-apr/injection-aids.html?referrer=https://www.google.com/, see exhibit cover sheet for details.
alibaba.com,1ml Fix Dose . . . https://www.alibaba.com/product-detail/1ml-Fix-Dose-immunization-AD-syringe_60103784550.html?s=p, see exhibit cover sheet for details.
horsewarehouse.com, Bio Sponge Paste . . . , http://www.horsewarehouse.com/cgi-bin/rtbin/rtl/phd.cgi?Autoincrement=000581&display_related=No, see exhibit cover sheet for details.
Mims, Eprex pre-filled inj 10000 IU/mL, https://www.mims.com/thailand/image/search/eprex?q=eprex, see exhibit cover sheet for details.
Al-Agzakhana, Enbrel (Etanercept) Injection . . . http://en.al-agzakhana.com/233/enbrel-etanercept-injection-uses-dosage-side-effects.html, see exhibit cover sheet for details.
alibaba.com, 30ml multi dose paste . . . https://www.alibaba.com/product-detail/30ml-multi-dose-paste-syringes-with_60488488120.html?s=p, see exhibit cover sheet for details.
drugs.com, Omontys, https://www.drugs.com/pro/omontys.html, accessed Dec. 14, 2017, see exhibit cover sheet for details.
Pharmacy & Purchasing Products, The Evolution of the CSTD, . . . Oncology Safety, vol. 12, No. 2, p. 1, https://www.pppmag.com/article/1638/, see exhibit cover sheet for details.
BD, BD Magni-Guide™ insulin syringe magnifier, http://www.bd.com/us/diabetes/page.aspx?cat=7002&id=7420, see exhibit cover sheet for details.
Abledata, Syringe Needle Guide and Vial Holder, http://www.abledata.com/indexing-terms/syringe-needle-guide-and-vial-holder, see exhibit cover sheet for details.
Diabetes Store, Vialdock Syringe Magnifier and Guide, https://www.diabetesstore.com/vialdock-syringe-magnifier-and-guide, see exhibit cover sheet for details.
Mallinckrodt Hemostat Solutions, Recothrom® Thrombin topical (Recombinant), http://www.hemostatsolutions.com/recothrom/Convenience, see exhibit cover sheet for details.
Imedez, Instructions for using advate, http://www.imedez.com/drugs/advate/Consumer-Medicine-Information.html, see exhibit cover sheet for details.
Adelphi Healthcare Packaging, MixJect, https://adelphi-hp.com/products/needleless-devices/mixject, see exhibit cover sheet for details.
MixJect, Instructions for Use, https://adelphi-hp.com/assets/files/mixject_instruction_sheet.pdf, see exhibit cover sheet for details.
medonthego.com, . . . , https://www.medonthego.com/Needle-20G-1-Inch-Hinged-Safety-Smiths-Medical-Needle-Pro-4285-Bx100_p_124574.html, see exhibit cover sheet for details.
Risperdal Consta®, . . . for Use, http://www.janssencns.com/risperdal/bipolar-i-disorder/dosing-and-administration/instructions-for-use, see exhibit cover sheet for details.
Rexlist, Xyntha, https://www.rxlist.com/xyntha-drug.htm, see exhibit cover sheet for details.
Google, Ultrasite Vial Adapter Pins/Vial Adapters BMG412012 B Braun Medicalhttps://www.google.com/imgres?imgurl=http%3A%2F%2Fsite . . . , see exhibit cover sheet for details.
ISIP. Vial Adapters, http://www.isips.org/page/safety_products/vial_adapters, see exhibit cover sheet for details.
Braun, Vented Spike Adaptor, http://www.bbraunusa.com/products.html?prid=418105, see exhibit cover sheet for details.

* cited by examiner

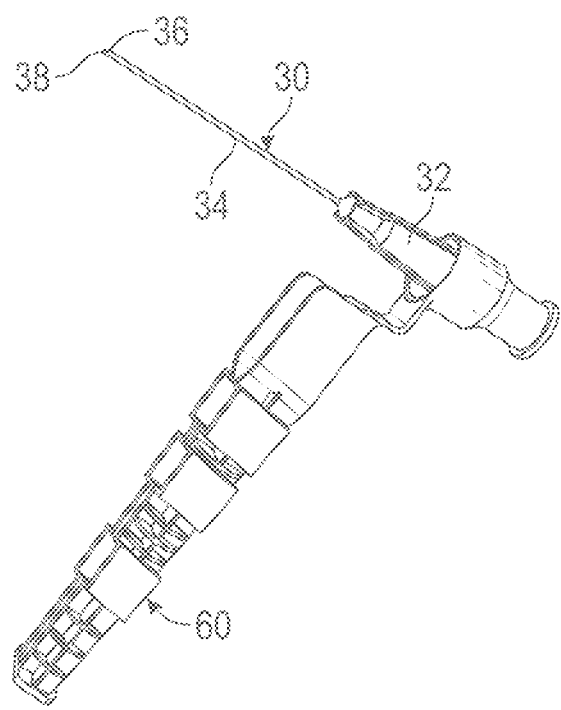
FIG. 4
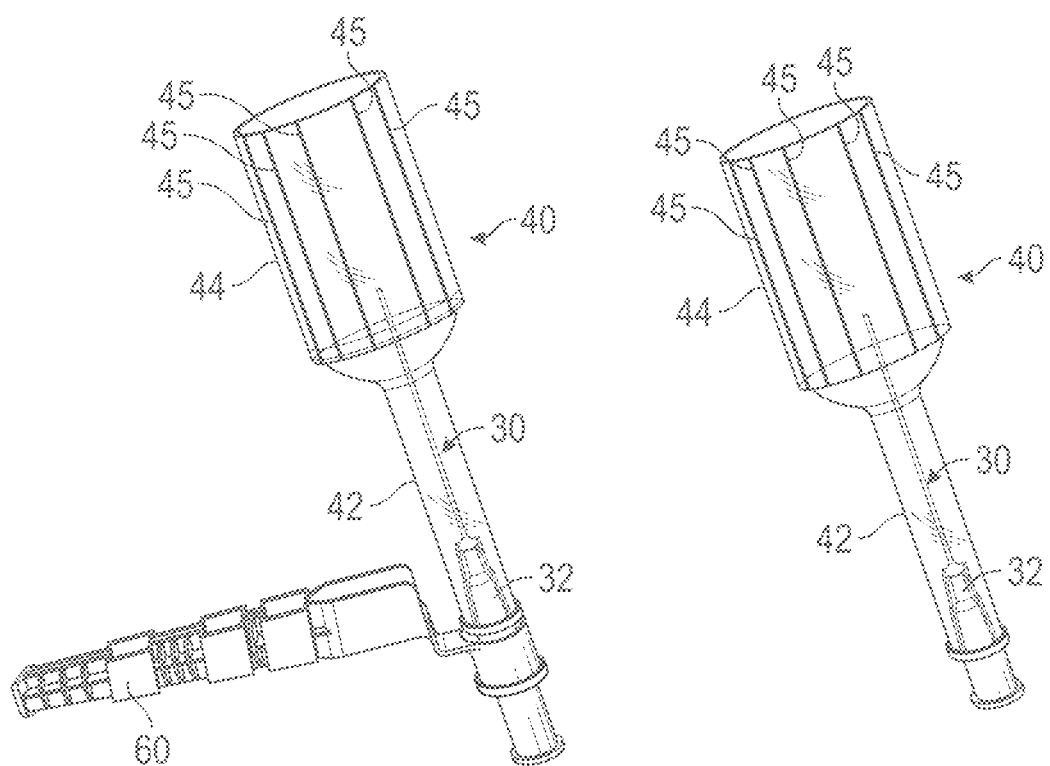
FIG. 5A
FIG. 5B

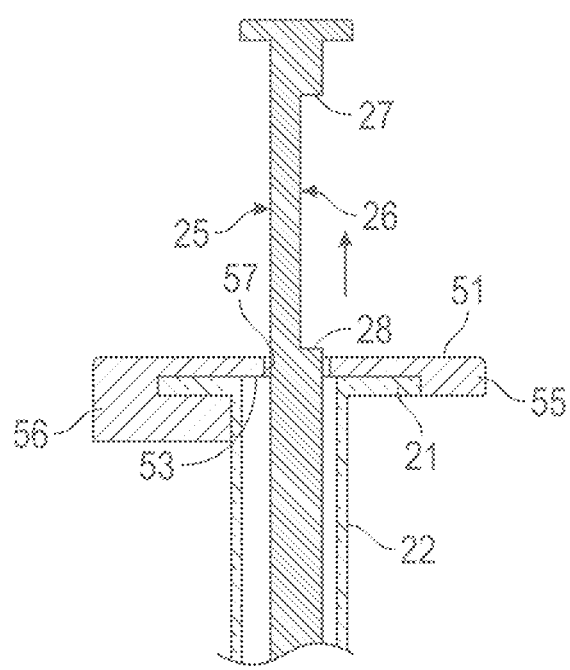
FIG. 12F
FIG. 12H
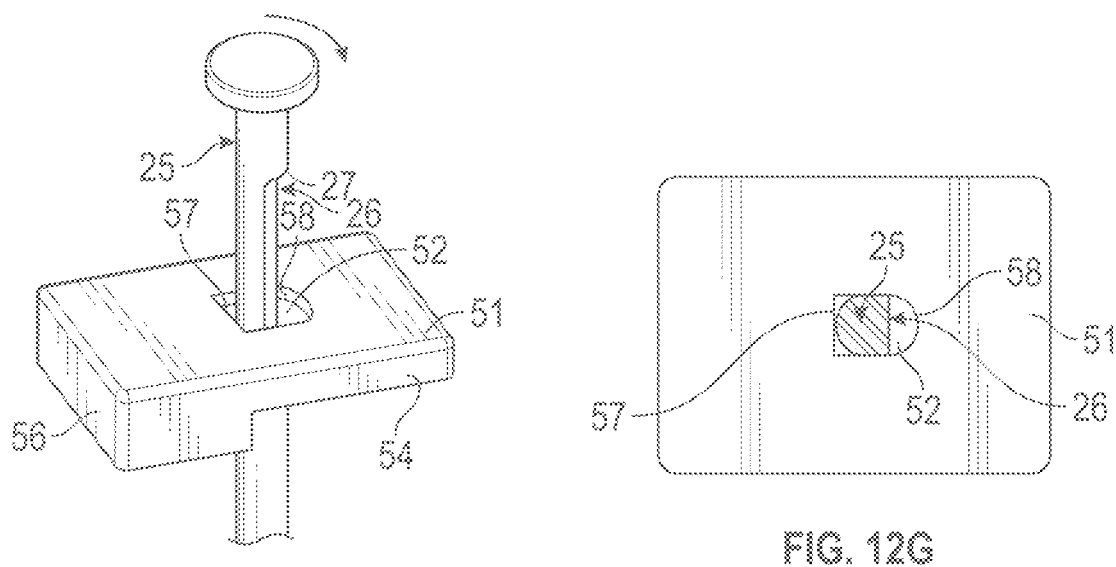
FIG. 12G
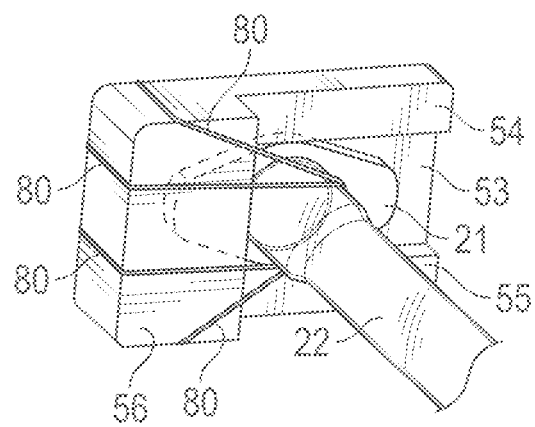
FIG. 13A
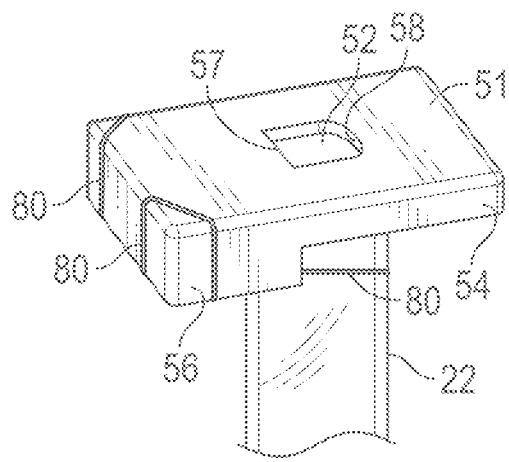
FIG. 13B

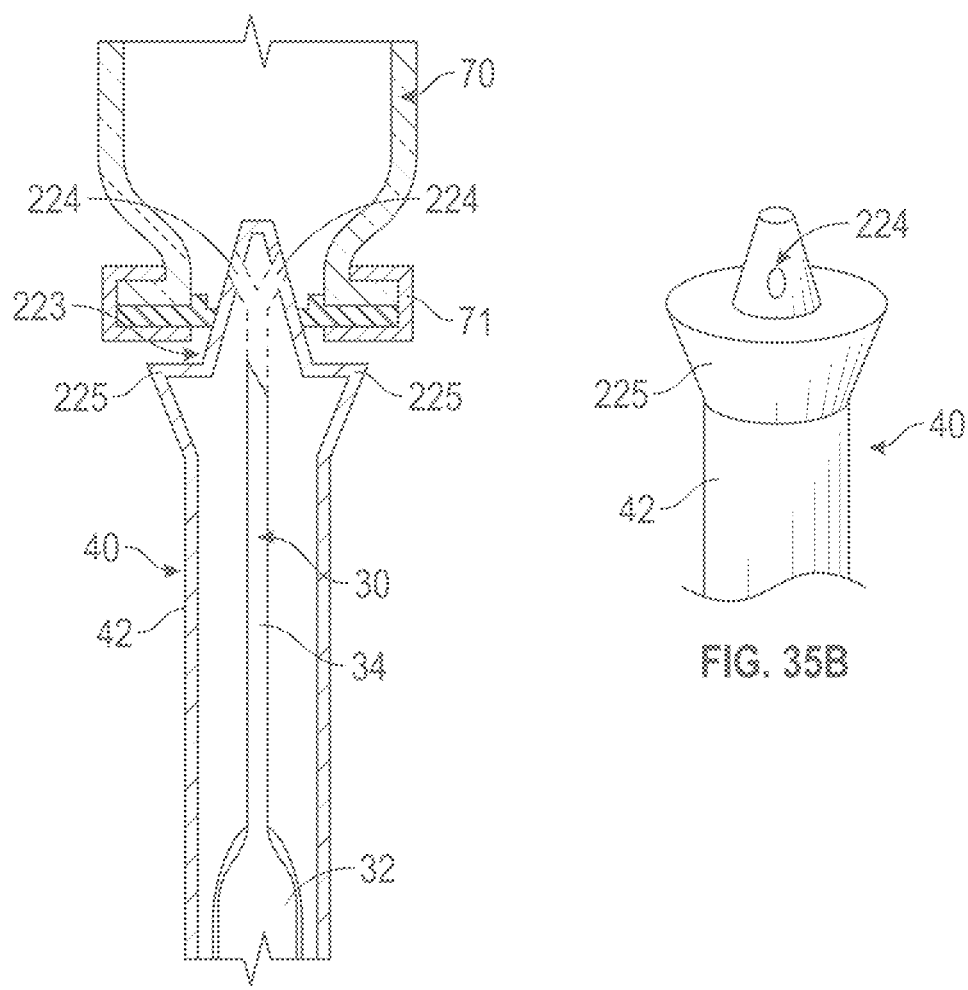
FIG. 35A
FIG. 35B
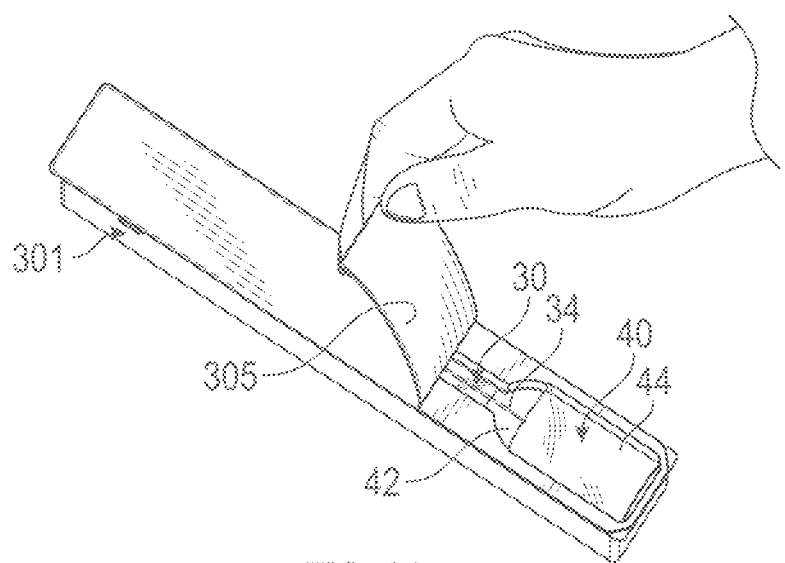
FIG. 36

METHODS, SYSTEMS AND DEVICES FOR ADMINISTERING MEDICATION

CROSS-REFERENCE TO RELATED APPLICATIONS

The present patent document claims the benefit of and priority to:
U.S. Provisional Patent Application Ser. No. 62/396,101, entitled "Enhanced System for Administration of Injectable Medications", filed on Sep. 17, 2016, the entire contents of which is hereby incorporated by reference as part of this application.

BACKGROUND

Technical Field

The disclosure relates at least to methods, systems and devices for administering medication.

Discussion of Related Field

Many people have medical conditions that require regular, emergency or otherwise administration of medicines to themselves or by others.

In general terms, adverse working conditions may make administering injectable medication difficult. Adverse working conditions may include low lighting, bad weather, wearing winter gloves and other clothing or equipment, poor eyesight, unfamiliarity, ambulatory motion, stress, high-volume vaccinations, and other conditions that may make it difficult to handle, read (such as reading the graduation, if any, on a syringe) or otherwise administer medication. There is at least a need for improved medication delivery devices, methods and systems that allow a user to more easily administer medication under adverse working conditions.

Administering too much or too little medication may be harmful to patients. Current approaches to administering medication may require fine measurements and good eyesight to ensure accurate dosage (such as drawing a plunger to a specific graduation). Adverse working conditions, such as those indicated above, may make it difficult to administer medication accurately. As such, there is at least a need for improved medication delivery devices, methods and systems that may ensure that the correct dosage is administered, that prevent overdosing and that reduce the need for a user to exercise fine motor skills and good eyesight to ensure accurate dosage.

Current approaches to administering medication may require a user to be trained in order to properly use current approaches to administering medication. As such, there is at least a need for improved medication delivery devices, methods and systems that may be used by individuals with limited training (such as diabetics giving themselves insulin injections or anemia patients giving themselves routine B12 injections).

Current approaches to administering medication may allow individuals to use the same needle to access and extract medication from the vial and inject it. However, such approaches may use unshielded needles which run the risk of being damaged (such as being brokers or bent), causing damage to others (such as sticking individuals administering the medication) or being contaminated. Damaged and contaminated needles and inadvertent needle-sticks necessitate changing the needle before injecting. Not only does such waste resources but it may cost valuable time, especially in adverse working conditions (such as emergency situations). Furthermore, if one uses rubber-septum vials, under current approaches one may need to use an unshielded needle to access the medication while taking care not to blunt or bend the needle through mishandling. There is at least a need for improved medication delivery devices, methods and systems that allow a user to use a shielded needle when administering medication in order to reduce or eliminate the risk of causing damage to the needle and others, or of being contaminated.

Current approaches to administering medication may require the needle to be carefully held in the vial below the medication level. Fine motor skills and other skills may be required to perform such approaches, which requirement may be hampered by adverse working conditions, especially in crisis or emergency situations. There is at least a need for improved medication delivery devices, methods and systems that reduce the level of fine motor skills a user must exercise when securing the needle in the vial below the medication level, including under adverse working conditions.

With regards to drawing a dose with a standard syringe, current approaches may require a user to properly center a needle in three dimensions and push all the way through the septum of the vial while taking care not to blunt the needle on the bottom or sides of the vial. The user may be required to push air into the vial to relieve the vacuum and draw back while watching the graduations. As such, there is at least a need for improved medication delivery devices, methods and systems that center the needle in the vial, set the tip at the proper depth and stop retraction at the appropriate volume to prevent overdosing.

Current approaches to administering medication may use a vial access or guiding device to access a vial and a needle to inject the medication. However, in order to use currently available vial access or guiding devices for non-IV (or non-port) injections, the vial access or guiding devices must be removed from the syringe and a separate needle must then be attached to the syringe before injecting a patient. Having to both remove the vial access or guiding device and then attach the needle takes additional time, requires an additional step and may increase the possibility of error, damage and contamination. As such, there is at least a need for improved medication delivery devices, methods and systems that configure the needle and the vial access or guiding device in such a way that eliminates the need to attach the needle to the syringe after the vial access or guiding device has been used and before injecting the patient.

Current auto-injectors may include instructions to press the auto-injector firmly against the injection site. Such instructions may often be misinterpreted by end-users who overenthusiastically hitting or otherwise engage the auto-injector against the site, resulting in additional pain and possible contusions to the patient. As such, there is at least a need for improved medication delivery devices, methods and systems that use a manual injection process wherein end-users may be less likely to make such mistakes.

Current auto-injectors and cartridge-based systems may be expensive and complex mechanisms. Auto-injections or cartridge-based systems may pose a risk of being misused. As such, there is at least a need for improved medication delivery devices, methods and systems that may be simple to use and manufacture, less expensive and safer.

Current prefilled syringes, auto-injectors and cartridge-based systems may exist for one-dose injections and may be limited in flexibility to only what is available from specific manufacturers. As such, there is at least a need for improved medication delivery devices, methods and systems that may use inserts, flexible guiding elements, adaptable components or other configurations to allow use with any vial.

In light of the above, there is a need for improved medication delivery devices, methods and systems that at least provide a syringe, a needle, a vial access or guiding device and a medication volume limiting device which ensure the correct placement of the needle in the vial, secure the operable connection of the needle and vial while medication is being extracted from the vial, protect the needle from being damaged or causing damage, limit the amount of medication that may be administered and ensure that patients are given the correct dosage without having to rely on graduations on the syringe (if any), that may be used by individuals with limited training under adverse working conditions, and that otherwise overcome at least some of the disadvantages and needs stated and apparent above.

SUMMARY

In one aspect of the disclosure, a medication delivery device may include: a syringe, including: a flange, a syringe barrel for housing medication, a plunger slideably disposed in the syringe barrel for drawing medication from a vial into the syringe barrel and for injecting the medication from the syringe barrel into a patient, wherein at least a portion of the plunger may be configured for limiting the distance the plunger can travel within the syringe barrel; and a syringe tip; a needle; a guiding element comprising a guiding element shaft for housing the needle, and a volume limiter for limiting the amount of medication that can be drawn from the vial.

Implementations may include one or more of the following features. The medication delivery device may include a safety sleeve for covering the needle, wherein the safety sleeve may be operably connectable to the syringe and the needle. The guiding element may operably connect to the needle and include a guiding element barrel for securing the vial and for guiding the needle into the vial. The volume limiter may operably connect to the syringe. The volume limiter may include a top surface; a bottom surface; an opening through which the plunger may be inserted; a first bottom ledge and a second bottom ledge arranged to allow the flange to slide in between and be secured by the first bottom ledge and the second bottom ledge; and a first flange housing element for engaging the flange. The plunger may include an engagement section for limiting the distance the plunger can travel within the syringe barrel; and the volume limiter may include a top surface; a bottom surface; and an opening through which the plunger may be inserted, wherein the opening may include a first surface that assumes the contour of the engagement section of the plunger; and a second surface that assumes the contour of a surface of the plunger alternate to the engagement section. The plunger may include an engagement section for limiting the distance the plunger can travel within the syringe barrel, wherein the engagement section may include a second end that engages the volume limiter to limit the amount of medication that can be drawn from the vial. The plunger may be configured to disengage the second end from the volume limiter, thereby allowing plunger to travel without being restricted by the volume limiter. The plunger may include a channel and the volume limiter may include a pin, wherein the pin may interact with the channel to limit the distance the plunger can travel within the syringe barrel and to limit the amount of medication that can be drawn from the vial. The volume limiter may include a retention member for resiliently securing an operable connection between the volume limiter and the syringe and for automatically engaging the volume limiter to limit the amount of medication that can be drawn from the vial. The volume limiter may be permanently connected to the syringe and include a first flange housing element for engaging the flange; and a second flange housing element for engaging the flange. The volume limiter may include a swivelable plate which engages the engagement section of the plunger to limit the amount of medication that can be drawn from the vial. The volume limiter may be configured into the syringe barrel as at least one protrusion which may engage a second end of the plunger to limit the distance the plunger may travel within the syringe barrel and to limit the amount of medication that can be drawn from the vial. The guiding element shaft may be configured as a semi-sharp cannula and include a neck designed to be sharp enough to puncture a rubber septum of the vial but not sharp enough to penetrate skin; and at least one duct wherein medication may flow from the vial to the needle. The medication delivery device may include a venting needle for allowing air into the vial as medication may be withdrawn from the vial in order to prevent the formation of a vacuum that may inhibit flow of medication into the syringe. The guiding element may include at least one flexible member for engaging and securing the vial when the vial is inserted into the guiding element barrel. The medication delivery device may include a means for guiding the needle into substantially the center of the vial; and a means for automatically engaging the volume limiter for limiting the amount of medication that can be drawn from the vial. The medication delivery device may include a means for engaging vials of more than one size.

In one aspect a method for administering medication using a medication delivery device which may include: a syringe which may include a flange; a syringe barrel for housing medication; a plunger slideably disposed in the syringe barrel for drawing medication from a vial into the syringe barrel and for injecting the medication from the syringe barrel into a patient, wherein at least a portion of the plunger is configured for limiting the distance the plunger can travel within the syringe barrel; and a syringe tip; a needle; a guiding element which may include a guiding element shaft for housing the needle; and a guiding element barrel for securing the vial and for guiding the needle into the vial; a volume limiter for limiting the amount of medication that can be drawn from the vial, wherein the method for administering medication using the medication delivery device may include: inserting the vial into the guiding element barrel such that the needle accesses the vial below the medication level; drawing back on the plunger to fill the syringe with medication until the volume limiter prevents further travel of the plunger, removing the guiding element and the vial from the needle to expose the needle; inserting the needle into the patient; depressing the plunger to inject the medication into the patient; and withdrawing the medication delivery device from the patient.

In another aspect a method for administering medication using a medication delivery device which may include: a syringe which may include a flange; a syringe barrel for housing medication; a plunger slideably disposed in the syringe barrel for drawing medication from a vial into the syringe barrel and for injecting the medication from the syringe barrel into a patient, wherein at least a portion of the plunger is configured for limiting the distance the plunger can travel within the syringe barrel; and a syringe tip; a needle; a guiding element which may include a guiding element shaft for housing the needle; and a guiding element barrel for securing the vial and for guiding the needle into the vial; a volume limiter for limiting the amount of medication that can be drawn from the vial; wherein the method for administering medication using the medication delivery device may include inserting the vial into the guiding element barrel such that the needle accesses the vial below the medication level; depressing the plunger to force air into the vial; allowing the plunger to automatically draw back to fill the syringe with medication until the volume limiter prevents further travel of the plunger; removing the guiding element and the vial from the needle to expose the needle, inserting the needle into the patient; depressing the plunger to inject the medication into the patient; and withdrawing the medication delivery device from the patient.

These general and specific aspects may be implemented by using systems, apparatuses, devices, means, methods and structures and/or any combination thereof.

Certain implementations may provide one or more of the following advantages. Embodiments may not achieve any or all of the listed advantages. Further, this is not an exhaustive list of all possible advantages of the disclosure. One or more embodiments of the disclosure may be configured to be and/or provide users the following.

In one or more embodiments, the disclosure may prevent accidental overdosing, in one or more embodiments, the disclosure provides a volume limiter or a physical barrier to overdosing, thereby providing a safe process that ensures the correct dosage is administered. In one or more embodiments, the disclosure may include a syringe with a pre-attached needle and a fixed volume limiter to prevent accidental overdosing.

In one or more embodiments, the disclosure may provide for a manual delivery system for medications to be administered by persons with limited training.

In one or more embodiments, the disclosure, when compared to conventional ways of administering medication, may do one, some, none or a combination of the following: eliminate steps when administering medication, eliminate fine measurement steps when administering medication in order to ensure accurate dosage, and reduce costs by eliminating the engineering and materials involved in providing accurate doses.

In one or more embodiments, the disclosure may provide for a safe, convenient, simple, and cost effective means for administering medication. In one or more embodiments, the disclosure may be simple and low cost to manufacture and may be sold at an affordable price and inexpensive to replace. In one or more embodiments, the disclosure may be designed to make the process safe for field use.

In one or more embodiments, the expiration date of the disclosure may not be dependent upon the expiration date of the medication that is to be administered to patients. In one or more embodiments, a patient may be able to replace outdated medication without having to replace the disclosure, thereby allowing users to keep quality medication on hand without having to incur the additional expense of replacing the disclosure. In one or more embodiments, the disclosure may be provided or sold independent of the medication being administered to minimize costs, eliminate short expiration dates and allow the disclosure to be used for administering different medications.

In one or more embodiments, the disclosure may be designed to be easy to use and safe to the individual administering the medication. In one or more embodiments, the disclosure may be designed such that a user is not likely to misuse it (such as using it backwards as is the case with EpiPen injectors) or spend unrecoverable dosage.

In one or more embodiments, the disclosure may be light weight. For example, in one or more embodiments, for about the same weight and general size as a twin-pack of EpiPen injectors, a patient may carry enough of the disclosures and a 1 mL vial of epinephrine to provide up to three doses for adults or six doses for pediatric patients.

In one or more embodiments, the disclosure may be produced in an array of sizes (such as designed to carry a variety of dosages). In one or more embodiments, the disclosure may be able to be used for virtually any type of medication. In one or more embodiments, the disclosure may be designed to be used with multi-dose vials.

In one or more embodiments, the disclosure may be designed to replace regular needle/syringe sets used for IM or SC injections.

Other aspects and advantages may be apparent from the following detailed description, the accompanying drawings, and the claims.

BRIEF DESCRIPTION OF THE DRAWINGS

Various embodiments of the disclosure will now be discussed with reference to the appended drawings. It is appreciated that these drawings depict only typical embodiments of the disclosure and are not to be considered limiting of its scope.

FIG. 4 shows a perspective view of one embodiment of a needle operably connected to one embodiment of a safety sleeve;

FIG. 5A shows a perspective view of one embodiment of a guiding element and one embodiment of a safety sleeve;

FIG. 5B shows a perspective view of one embodiment of a guiding element;

FIG. 12F shows a perspective view of the embodiment of the plunger illustrated in FIG. 11A inserted through an opening and twisted;

FIG. 12G shows a top view of a sectional view of the embodiment of the plunger illustrated in FIG. 11A inserted through an opening and twisted;

FIG. 12H shows a sectional view of the embodiment of the plunger illustrated in FIG. 11A inserted through an opening and twisted;

FIG. 13A shows a bottom perspective view of the configuration illustrated in FIG. 10D, albeit the volume limiter shown in FIG. 13A includes a retention member;

FIG. 13B shows a top perspective view of the embodiment of the volume limiter illustrated in FIG. 13A;

FIG. 35A shows a cross sectional view of the embodiment of the guiding element illustrated in FIG. 34A, albeit a neck assumes a cone configuration and a duct assumes a "Y" configuration and only a single needle is present;

FIG. 35B shows a perspective view of the embodiment of the guiding demerit illustrated in FIG. 35A;

FIG. 36 shows a perspective view of one embodiment of a medication delivery device in a blister package.

DETAILED DESCRIPTION

Figure 1:
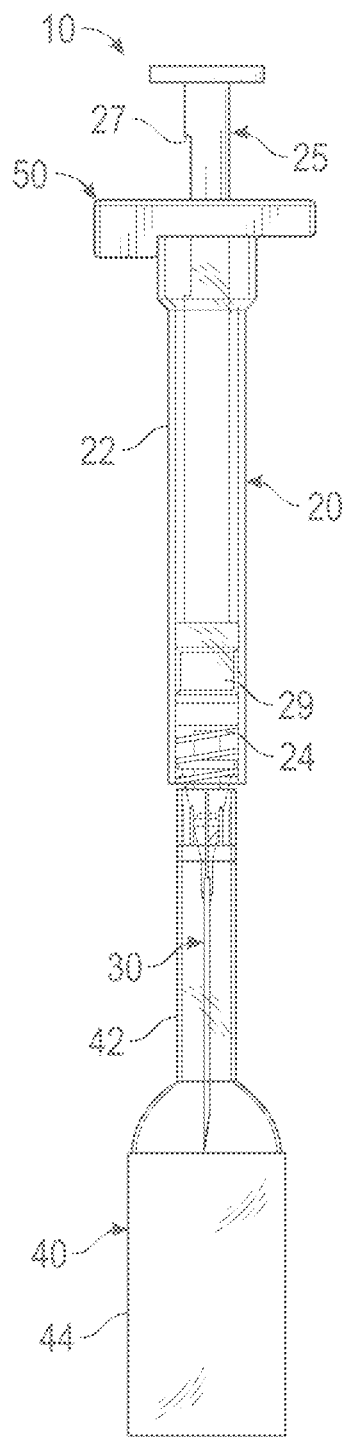
FIG. 1 shows a side view of one embodiment of a medication delivery device.

The following description illustrates principles of the disclosure which may be applied in various ways to provide different embodiments. There may be many different forms of embodiments of the disclosure, and as such, embodiments should not be limited to those set forth herein and shown in the accompanying drawings. While exemplary embodiments of the disclosure may be shown and described herein, changes and modifications may be made without departing from its scope and concepts. That which is set forth herein and shown in the accompanying drawings is offered to illustrate the principles of the disclosure and not as limitations. Other variations of the disclosure may be included within the principles of the disclosure.

In some embodiments, the disclosure may be configurable, adaptable and customizable to meet the various needs of various users in various circumstances and to be compatible and used in conjunction with various systems, apparatuses, articles, devices, means, methods and structures. The disclosure may be used for various uses and for various purposes. For example, the disclosure may be used to administer medication to people, animals and things.

The disclosure may be configured in various ways, by various means and various methods, with various parts, to various dimensions (such as shapes, lengths, widths, heights, depths, and sizes) and with and from various materials, and any combinations thereof. The specific parts, materials, members, devices, systems and components of the disclosure may be configured together or separate and with other parts, materials, members, devices, systems and components and any combinations thereof. In one or more embodiments, one or more aspects of the disclosure may be configured in various ways including, for example, but not limited to being configured together or separate, releasably or non-releasably.

The drawings herein may but do not necessarily illustrate the disclosure to scale. The drawings herein may but do not necessarily depict the exact positions, shapes, sizes, layouts, designs, angles and other dimensions and configurations in which the disclosure may be implemented. In one or more embodiments, the components of the disclosures may be configured to various positions, shapes, sizes, layouts, designs, angles and other dimensions and configurations from various materials, for various reasons.

At least some components of the disclosure may be formed from various materials. For example, in one or more embodiments, the material used to make the disclosure may include metals (such as aluminum, silver, gold, europium, neptunium, cobalt, iron, cooper, nickel, lead, lithium, calcium, titanium, tin, etc.), non-metals (such as carbon, sulfur, chlorine, argon, etc.), metalloids (such as boron, tellurium, etc.), ceramics (such as alumina, silicon, tungsten, granite, limestone, marble, slate, quartzite, etc.), polymers and plastics (such as natural rubbers, synthetic rubbers, polyvinyl chloride (PVC), PC, high density polyethylene (HDPE), oriented or stretch blown polyethylene terephthalate (PET), polypropylene (PP), acrylonitrile butadiene styrene (ABS), polycarbonate, etc.), alloys (such as alloys of aluminum, alloys of bismuth, alloys of chromium, alloys of cobalt, alloys of copper, alloys of gallium, alloys of gold, alloys of indium, alloys of iron, alloys of lead, alloys of magnesium, alloys of mercury, alloys of nickel, alloys of plutonium, alloys of potassium, rare earth alloys, alloys of rhodium, alloys of scandium, alloys of silver, alloys of sodium, alloys of titanium, alloys of tin, alloys of uranium, alloys of zinc, alloys of zirconium, etc.), woods and natural products (such as hickory, aspen, maple, cedar, spruce, hemlock, pine, oak, walnut, elm, fir, mahogany, kunststoff, cotton, flax, wool, ramie, silk, yarn, denim, corduroy, leather, suede, down, fur, bamboo, jute, etc.), and the like and other materials may be used to make at least some components of the disclosure. In one or more embodiments, components of the disclosure may be made from non-degradable materials (such as glass, stainless steel, titanium, etc.) and degradable or self-dissolving materials (such as sugar and sugar derivatives). In one or more embodiments, components of the disclosure may be made from injection molds.

FIG. 1 shows a side view of one embodiment of a medication delivery device 10 which may be designed for the purpose of administering medication. In one or more embodiments, medication delivery device 10 may be configured to facilitate easy and quick access to multi-dose medication vials and a syringe with a fixable volume to ensure proper dosage, prevent overdosing and minimize fine measurements required to be performed by a user. In one or more embodiments, medication delivery device 10 may be designed to provide an inexpensive and flexible alternative to auto-injectors or cartridge-based or other systems while facilitating use and preventing injury to caregivers with limited training, such as family members or patients, as well as trained caregivers in adverse working conditions, such as emergency medical personnel in moving ambulances. In one or more embodiments, medication delivery device 10 may be configured to ensure the correct placement of a needle in a vial, secure the operable connection of the needle and vial while medication is being extracted from the vial, protect the needle from being damaged or causing damage, limit the amount of medication that may be administered and ensure s that patients are given the current dosage without having to rely on graduations on the syringe (if any), that may be used by individuals with limited training under adverse working conditions.

In one or more embodiments, medication delivery device 10 may be used by various individuals. For example, medication delivery device 10 may be used by a person administering medication to him or her-self or by a person administering medication to another, such as by family members, friends, caretakers and other non-medical professionals, as well as by medical professionals, such as nurses, doctors, dentists, veterinarians and other medical professionals.

In one or more embodiments, medication delivery device 10 may be used in various environments and under various conditions. For example, medication delivery device 10 may be used in emergency medical services, such as in the emergency room or ambulatory setting, the doctor's office, the surgery room, the veterinarian's clinic or on the farm. In the home health services, etc. In one or more embodiments, medication delivery device 10 may be used when the user is hampered by adverse working conditions, including crisis or emergency situations, ambulatory settings, low lighting, bad weather, poor eyesight, unfamiliarity, wearing winter gloves or other clothing or equipment, high-volume vaccination settings, and other conditions that, may make it difficult to handle or read or otherwise administer the medication.

In one or more embodiments, medication delivery device 10 may be simple and low cost to use and manufacture. In one or more embodiments, medication delivery device 10 may be manufactured for little more than a standard syringe and needle set. In one or more embodiments, medication delivery device 10 may lower the skill level needed to operate it properly, and thereby expand access to inexpensive injectable medications for various uses, such as home care settings. In one or more embodiments, medication delivery device 10 may be designed to remove much of the fine motor skill required under current approaches and thereby make high-volume use more efficient.

In one or more embodiments, medication delivery device 10 may be simple and safe to use and convenient. In one or more embodiments, medication delivery device 10 may be designed such that a user is unlikely to misuse (such as using it backwards) or spend an unrecoverable dose. In one or more embodiments, medication delivery device 10 may be configured to an array of sizes capable of administering various dosages. In one or more embodiments, at least some components of medication delivery device 10 may be disposable or reusable, single-use or multi-use, or a combination thereof.

In one or more embodiments, medication delivery device 10 may be configured to inject medication into a patient, in various locations on the patient's body. For example, medication delivery device 10 may be adapted to administer medication intradermally, intravenously (IV), subcutaneously (SC), intramuscularly (IM), intraperitoneally (IP), intracardially, intraarticularly, intrathecally, and in other locations. In one or more embodiments, medication delivery device 10 may be configured to removed fluid from patients and administer medication orally.

In one or more embodiments, medication delivery device 10 may be used to administer various types of medication. For example, in one or more embodiments, medication delivery device 10 may be used for patients needing injections for vitamin B12, insulin, epinephrine, vaccinations, adenosine or any other injectable medication.

As shown in FIG. 1, in one or more embodiments, medication delivery device 10 may include a syringe 20, a needle 30, a guiding element 40, and a volume limiter 50.

In one or more embodiments, syringe 20 may assume various configurations and be formed from various materials for various purposes, including for the purposes of holding and administering a variety of volumes of medication or other liquids or gases. In one or more embodiments, syringe 20 may be configured to hold microliters, milliliters or liters, or combinations thereof. For example, syringe 20 may hold between about 0.5 µL to about 2 L (such as 1 ml, 3 ml, 5 ml, 10 ml and 20 ml) of medication depending on the level of dosage needed or other desired outcomes. In one or more embodiments, syringe 20 may be designed to be transparent in order to visualize the level of medication. In one or more embodiments, syringe 20 may designed to be non-transparent. In one or more embodiments, syringe 20 may include graduation markings to indicate the level of medication contained in syringe 20. In one or more embodiments, syringe 20 may be configured in the form of a hypodermic syringe, insulin syringe, microinjector, tuberculin (TB) syringe, LT syringe, TLL syringe, specialty syringes, etc. As shown in FIG. 1, in one or more embodiments, syringe 20 may include various components, such as a flange 21 (not shown in FIG. 1), a syringe barrel 22, a syringe tip 24 and a plunger 25.

Figure 2:
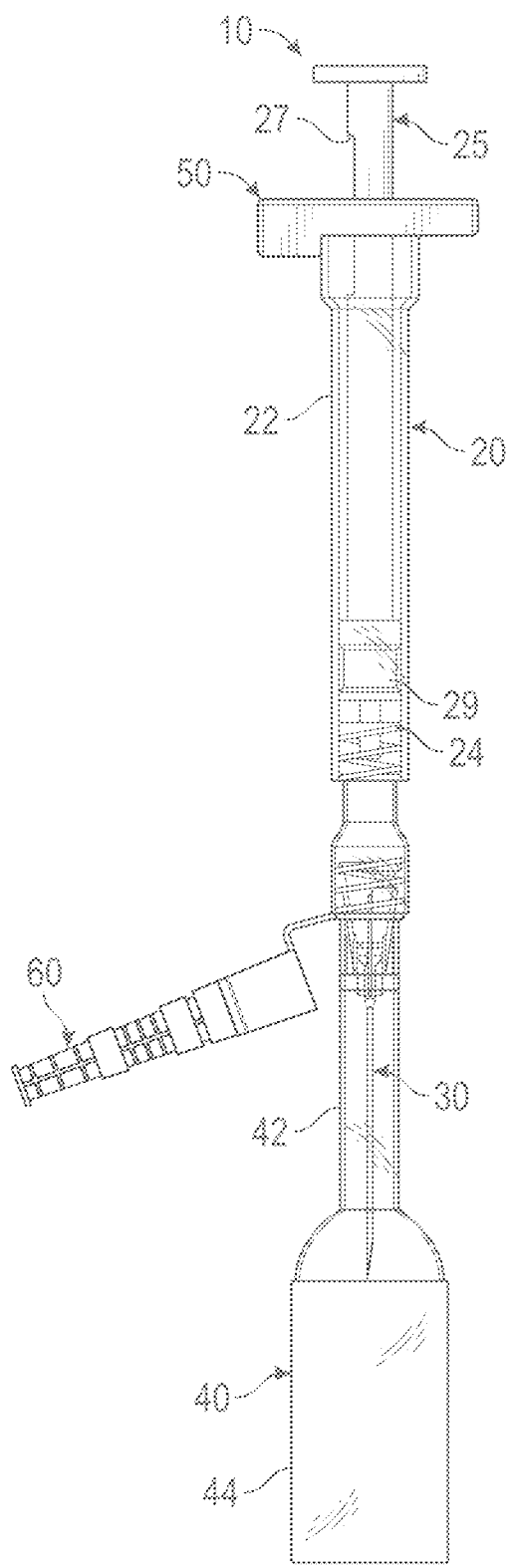
FIG. 2 shows a side view of one embodiment of a medication delivery device including a safety sleeve.

In one or more embodiments, flange 21 may assume various configurations and be formed from various materials for various purposes. For example, flange 21 may be configured to include a projecting rim or collar around one end of syringe 20. In one or more embodiments, volume limiter 50 may be operably connected to flange 21 and a user may engage the operably connected volume limiter 50 to aid in drawing, handling and injecting medication into a patient. In one or more embodiments, syringe barrel 22 may assume various configurations and be formed from various materials for various purposes, including for the purposes of intaking, holding and expelling medication or other liquids or gases. For example, syringe barrel 22 may be a cylindrical tube which allows plunger 25 to be slideably pulled and pushed along the inside surface of syringe barrel 22 in order to intake and expel substances. In one or more embodiments, syringe barrel 22 may be made from glass, plastic and/or other materials. In one or more embodiments, syringe barrel 22 may be transparent or non-transparent and may include volume markers. In one or more embodiments, syringe tip 24 may assume various configurations and be formed from various materials for various purposes. In one or more embodiments, syringe tip 24 may be configured as a Luer Lok tip wherein needle 30 may be twisted into syringe tip 24 for operably connecting syringe 20 to needle 30 or for operably connecting other components or devices (such as safety sleeve 60 as shown in FIG. 2). Although not shown in FIG. 1, in one or more embodiments, syringe tip 24 may be configured as a slip tip, an eccentric tip (which may be designed for administering medication close to the surface of the skin, such as artery injections or injections into veins), a catheter tip (which may be designed for irrigation purposes or to be used in conjunction with tubing) or other tip configurations. In one or more embodiments, syringe tip 24 may assume other configurations to be used in connection with various devices. In one or more embodiments, plunger 25 may assume various configurations and be formed from various materials for various purposes. For example, plunger 25 may be made from plastic, rubber or other materials or combinations thereof for the purposes of drawing and expelling medication or other substances into syringe barrel 22. In one or more embodiments, plunger 25 may be rebated, notched, grooved, angled, protruded, channeled, serrated, flattened, rounded, cruciformed, modified, shaped or otherwise configured at different locations or depths in order to accommodate different volumes. In one or more embodiments, a color coding system on plunger 25 and other components of medication delivery device 10 may be used. In one or more embodiments, plunger 25 may include a plunger stopper 29 for forming a tight seal between plunger 25 and syringe barrel 22. In one or more embodiments, plunger stopper 29 may assume various configurations and be formed from various materials for various purposes. For example, plunger stopper 29 may be made from plastic, rubber or other materials or combinations thereof.

In one or more embodiments, needle 30 may assume various configurations and be formed from various materials for various purposes. For example, in one or more embodiments, needle 30 may be configured to various thicknesses, gauges and lengths dependent on anticipated injection sites, the amount and viscosity of medication to be administered, and other factors. In one or more embodiments, needle 30 may be about a 2 gauge to about a 36-gauge needle. In one or more embodiments, needle 30 may be about ¼ of an inch to about 8 inches in length. In one or more embodiments, needle 30 may be configured as a microneedle, arrays of needles, a specialty needle or other needle types. In one or more embodiments, needle 30 may be designed to reach nearly to the bottom of an upright vial 70 or to penetrate just the septum of an inverted vial 70. In one or more embodiments, a sleeve or other device or means may shield needle 30 to prevent injury or damage to needle 30 and others. More will be discussed about needle 30 below.

In one or more embodiments, guiding element 40 may assume various configurations and be formed from various materials for various purposes. For example, in one or more embodiments, guiding element 40 may include a guiding element shaft 42 for housing and protecting needle 30 and a guiding element barrel 44 for securing or otherwise engaging vial 70 and guiding needle 30 into substantially the center of vial 70. In one or more embodiments, guiding element 40 may limit the depth to which needle 30 may be inserted into vial 70. In one or more embodiments, guiding element 40 may include a removable sleeve (such as guiding element shaft 42) to set the depth needle 30 may travel into vial 70. In one or more embodiments, guiding element shaft 42 may shield needle 30 in order to reduce or eliminate the risk of needle 30 being damaged or causing damage to users or others, or of being contaminated. In one or more embodiments, guiding element 40 may keep needle 30 from being blunted or inadvertently bent. In one or more embodiments, guiding element 40 may shield needle 30 to prevent accidental sticks by extending past the tip of needle 30. In one or more embodiments, guiding element 40 may assume a cup-like shape attached to the end of a cut-down needle shield. In one or more embodiments, guiding element 40 may replace a standard needle shield with a configuration that may be opened and expanded on one end to a diameter that allows vial 70 to be placed into it. In one or more embodiments, the expanded area of guiding element 40 may be minimized in order to stop vial 70 at a point that allows the bevel of needle 30 to pass through the septum but remained submerged in the medication as well as keeping it from contacting the sides of vial 70. In one or more embodiments, guiding element 40 may be designed to shield the user from broken glass, such as when a user uses a glass vial 70 wherein special filtered needles may be required. In one or more embodiments, guiding element 40 may or may not contain a venting needle 200 to prevent vacuum. In one or more embodiments, guiding element 40 may be removed after use in order to expose needle 30 and allow a user to inject a patient. In one or more embodiments, guiding element 40 may use the same needle 30 for injections as well as access vial 70 and therefore require no needle change before injections, thereby eliminating the need to manually attach needle 30 after using the guiding element 40 as needle 30 may be pre-attached. In one or more embodiments, guiding element 40 may use inserts, a sliding shield, springs, rollers, semi-flexible material, or other materials and configurations to accept varying sizes of vials 70. In one or more embodiments, guiding element 40 may be made from rubber, plastic, metal or other materials, or combinations thereof. More will be discussed about guiding element 40 below.

In one or more embodiments, volume limiter 50 may assume various configurations and be formed from various materials for various purposes, including for the purpose of limiting the amount of medication syringe 20 can draw from vial 70. In one or more embodiments, volume limiter 50 may be a single piece or device. In one or more embodiments, volume limiter 50 may include multiple components. In one or more embodiments, volume limiter 50 may include at least one component that may be moveable relative to other volume limiter 50 components or other components of medication delivery device 10. In one or more embodiments, volume limiter 50 may be a slideable clip attachable to flange 21 of syringe 20, which syringe 20 may include a plunger 25 that may be rebated, notched, grooved, angled, protruded, channeled, serrated, flattened, rounded, cruciformed, modified, shaped or otherwise configured, though other methods, such as pins, detachable clips, and stops that engage plunger 25 may be configured. In one or more embodiments, volume limiter 50 may be designed as a slideable clip. In one or more embodiments, volume limiter 50 may include a rectangular piece configured to slide across the top of syringe 20 (such as flange 21) and a flat sided or otherwise shaped hole (such as an oblong hole) to engage a rebated, notched, grooved, angled, protruded, channeled, serrated, flattened, rounded, cruciformed, modified, shaped or otherwise configured section of plunger 25 (such as engagement section 26). In one or more embodiments, volume limiter 50 may automatically engage and include a spring to slide volume limiter 50 once the engagement section 26 of plunger 25 travels a certain distance. In one or more embodiments, volume limiter 50 may be adjustable to allow various dosages to be administered. In one or more embodiments, volume limiter 50 may be formed as a single clip design used for all volumes. In one or more embodiments, volume limiter 50 may be fixed or disengagable to allow for draw-back to check for "flash" upon injection. More will be discussed about volume limiter 50 below.

Although not shown in FIG. 1, medication delivery device 10 may include other components, for example, needle 30 may include a needle cap, cover, shield, sleeve, stop or safety cap for the purpose of covering the exposed portion of needle 30. In one or more embodiments, the disclosure may be light weight and compact. In one or more embodiments, medication delivery device 10 may be about 10 grams to about 15 grams in weight and about 6 inches to about 8 inches in length when fully assembled. In one or more embodiments, syringe 20 may be about 4 grams to about 6 grams in weight and about 4 inches to about 5.5 inches in length. In one or more embodiments, guiding element 40 may be about 4 grams to about 6 grams in weight and about 1.5 inches to about 2.5 inches in length. In one or more embodiments, volume limiter 50 may be about 1 gram to about 3 grams in weight, about 1 inch to about 1.5 inches in length and about 0.375 inch to about 0.5 inch in width, and about 0.15 inch to about 0.3 inch in depth.

Figure 3:
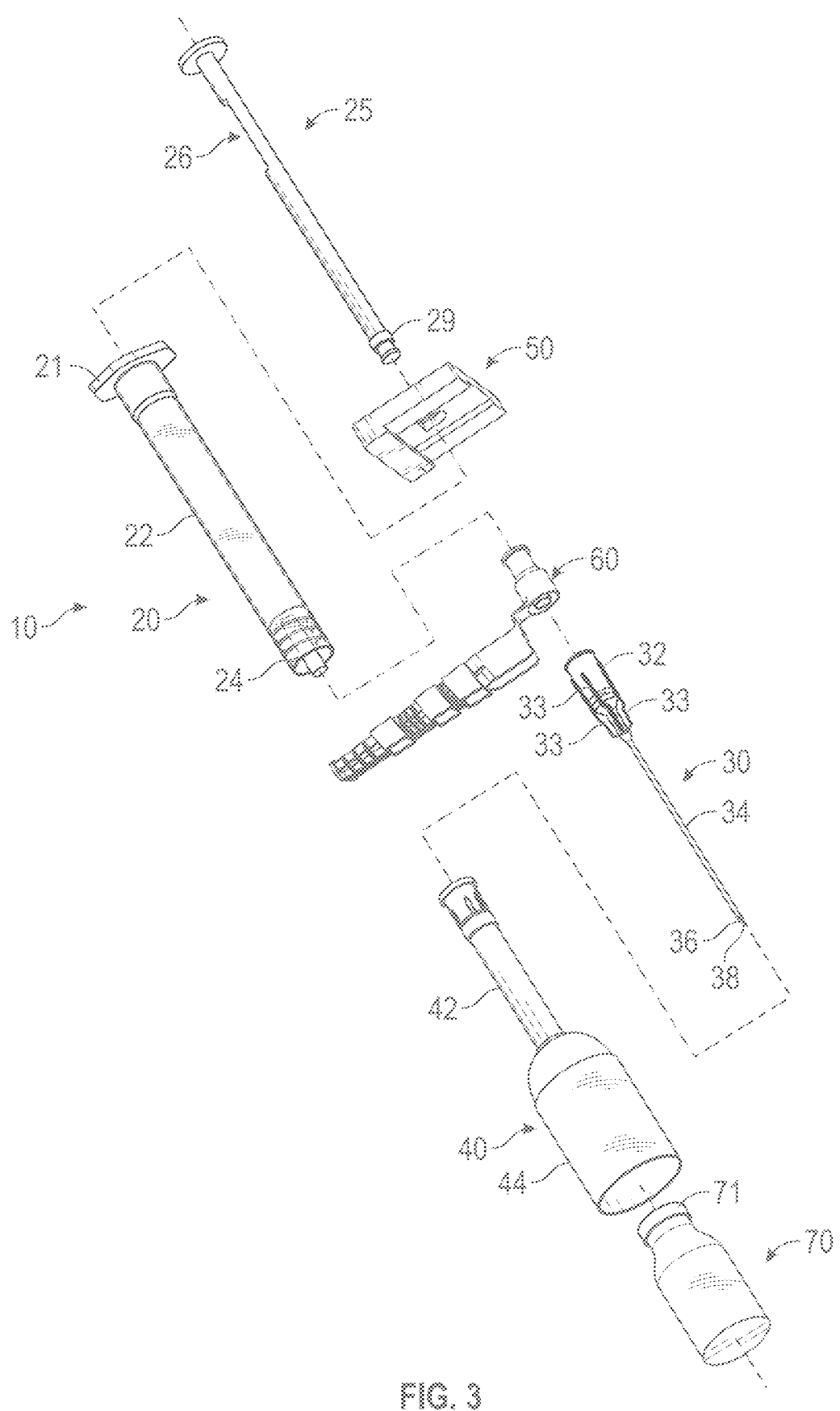
FIG. 3 shows an exploded perspective view of one embodiment of various components of a medication delivery device.

FIG. 2 shows a side view of one embodiment of medication delivery device 10 including syringe 20, needle 30, guiding element 40, volume limiter 50 and a safety sleeve 60. In one or more embodiments, needle 30 may be operably connected to safety sleeve 60 and safety sleeve 60 may be operably connected to syringe tip 24. In one or more embodiments, safety sleeve 60 may be configured to be articulatable relative to needle 30. In one or more embodiments, after administering medication, safety sleeve 60 may be designed to cover needle 30 in order to prevent further sticking, the spread of disease, and for other reasons. Although FIG. 2 shows safety sleeve 60 configured as a Protex Needle-Pro® device, in one or more embodiments, safety sleeve 60 may assume various configurations and be formed from various materials. In one or more embodiments, safety sleeve 60 may be sold or otherwise provided separately, FIG. 3 shows an exploded perspective view of one embodiment of various components of medication delivery device 10 including syringe 20, needle 30, guiding element 40, volume limiter 50 and safety sleeve 60. In one or more embodiments, medication delivery device 10 may provide a means for guiding needle 30 into substantially the center of vial 70 and for securing or otherwise engaging vial 70 while a user draws medication from it. For example, as indicated above, in one or more embodiments, guiding element 40 may include guiding element shaft 42 for housing and protecting needle 30 and guiding element barrel 44 for securing or otherwise engaging vial 70 and guiding needle 30 into substantially the center of vial 70. In one or more embodiments, vial 70 may be inserted into guiding element 40 which is configured to secure or otherwise engage vial 70 while medication is extracted from vial 70 into syringe 20. In one or more embodiments, once the medication has been extracted, guiding element 40 may be removed from medication delivery device 10 and the medication may be administered to the patient. In one or more embodiments, vial 70 may include a cap 71 which may include a rubber septum or stopper or other object or material through which needle 30 may be inserted to draw medication. In one or more embodiments, medication delivery device 10 may be compatible with standard multi-dose vials in widespread production. In one or more embodiments, medication delivery device 10 may be compatible with vials of various configurations and sizes and made from various materials (including glass, plastic and other materials). For example, vial 70 may be configured as a screw vial, lip vial, crimp vial, snap-top vial, hinged-capped vial or other configuration. As shown in FIG. 3, in one or more embodiments, needle 30 may include a hub 32, a shaft 34, a lumen 36 and a bevel 38. In one or more embodiments, the various components of medication delivery device 10 may be sold, manufactured or otherwise provided separately or operably connected together or a combination thereof. For example, syringe 20, needle 30 and safety sleeve 60 may be sold, manufactured or otherwise provided operably connected together, with guiding element 40 and volume limiter 50 provided unconnected. Alternatively and/or in addition, syringe 20, needle 30, guiding element 40, volume limiter 50 and safety sleeve 60 may be sold, manufactured or otherwise provided all operably connected together (as shown in FIG. 2). Alternatively and/or in addition, various other combinations of the connectivity of various components of medication delivery device 10, including other devices not shown herein, may be sold, manufactured or otherwise provided separately and/or operably connected together.

FIG. 4 shows a perspective view of one embodiment of needle 30 operably connected to one embodiment of safety sleeve 60. As shown in FIG. 4, and previously indicated, needle 30 may include hub 32, shaft 34, lumen 36 and bevel 38. In one or more embodiments, hub 32 may assume various configurations and be formed from various materials for various purposes. For example, hub 32 may be configured as a Luer Lock, hub for engaging with a corresponding element of safety sleeve 60. In one or more embodiments, a Luer Lock hub 32 configuration may provide an unacceptable volume of dead space leading to an about 0.1 mL shortage when a dose is drawn. To remedy such an issue, in one or more embodiments, needle 30 may be integral to syringe tip 24 to reduce the volume to a negligible level. Although not shown in FIG. 4, in one or more embodiments, hub 32 may be configured to engage syringe tip 24 directly. For example, as shown in FIG. 1, hub 32 may be configured as a Luer Lock hub for engaging with a corresponding Luer Lock syringe tip 24. Although not shown in FIG. 4, in one or more embodiments, hub 32 may be configured as a slip hub, metal hub, Kel-F hub, or other hub configurations. In one or more embodiments, hub 32 may include various materials (such as polypropylene) which may aid in performing hub's 32 desired function. In one or more embodiments, lumen 36 may define the diameter of the hole or gauge of needle 30 and bevel 38 may define that angle at which shaft 34 may be configured.

FIG. 5A shows a perspective view of one embodiment of guiding element 40 operably connected to and housing one embodiment of needle 30, which needle 30 is operably connected to one embodiment of safety sleeve 60. In one or more embodiments, once a user draws medication from vial 70, the user may remove guiding element 40, inject the medication into the patient, and then, optionally, articulate safety sleeve 60 and cover needle 30. Alternatively and/or in addition, in one or more embodiments, once a user draws medication from vial 70, the user may remove guiding element 40, inject the medication into the patient, and then, optionally, place guiding element 40 back over needle 30 for reuse, to cover needle 30 or for some other purpose.

FIG. 5B shows a perspective view of one embodiment of guiding element 40 operably connected to one embodiment of needle 30 without the presence of safety sleeve 60. In one or more embodiments, once a user draws medication from vial 70, the user may remove guiding element 40, inject the medication into the patient, and then, optionally, place guiding element 40 back over needle 30 for reuse, to cover needle 30 or for some other purpose. As shown in FIG. 5B and elsewhere, guiding element barrel 44 may be configured with ribbons 45 which may stabilize and reinforce the strength of guiding element barrel 44 and aid in its ability to resiliency secure vial 70. Although not shown in FIG. 5B, in one or more embodiments, guiding element barrel 44 may be configured without ribbons 45 (such as shown in FIGS. 1 and 2). In one or more embodiments, ribbons 45 may be configured substantially horizontally (instead of or in addition to substantially vertically as shown in FIG. 5B) on guiding element barrel 44.

Figure 6:
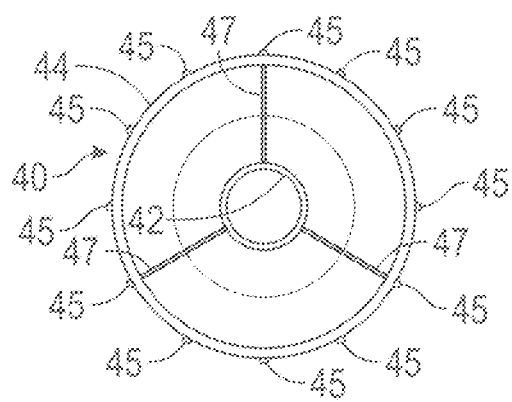
FIG. 6 shows a bottom view of one embodiment of a guiding element.

FIG. 6 shows a bottom view of one embodiment of guiding element 40. In one or more embodiment, the thickness of guiding element barrel 44 may vary and be adaptable for securing or otherwise engaging vial 70.

Figure 7:
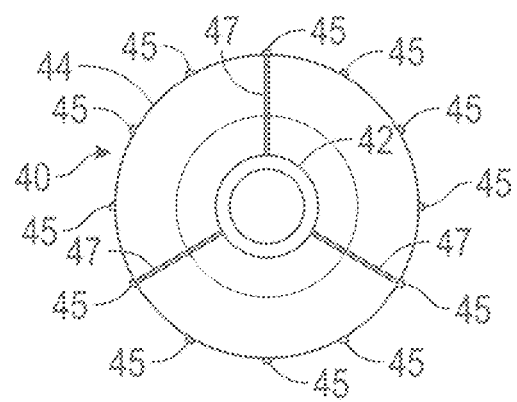
FIG. 7 shows a top view of one embodiment of a guiding element.

FIG. 7 shows a top view of one embodiment of guiding element 40.

Figure 8A:
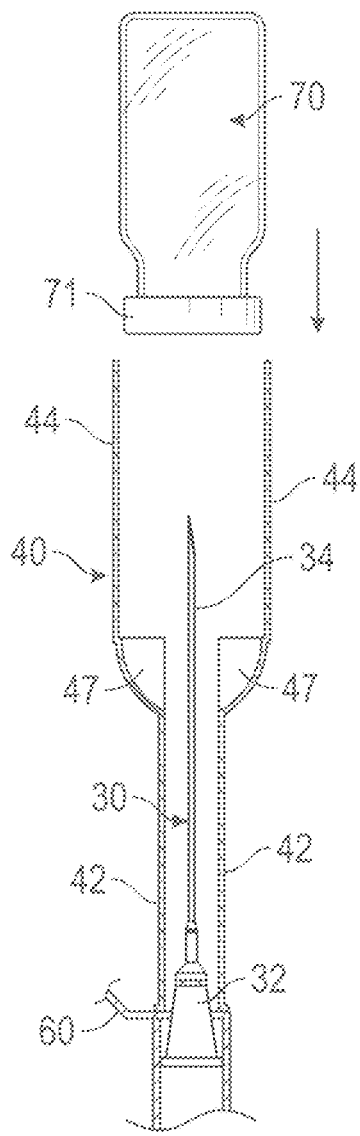
FIG. 8A shows a cross sectional view of one embodiment of a guiding element and one embodiment of a vial, wherein the vial is approaching the guiding element.

FIG. 8A shows a cross sectional view of one embodiment of guiding element 40, along with a side view of one embodiment of needle 30 and one embodiment of vial 70, wherein vial 70 is approaching guiding element 40. As shown in FIG. 8A, guiding element 40 may include at least three wings 47 (only two or the at least three wings 74 are shown in FIG. 8A) which may be designed to engage cap 71 of vial 70 and control the depth at which needle 30 accesses vial 70.

Figure 8B:
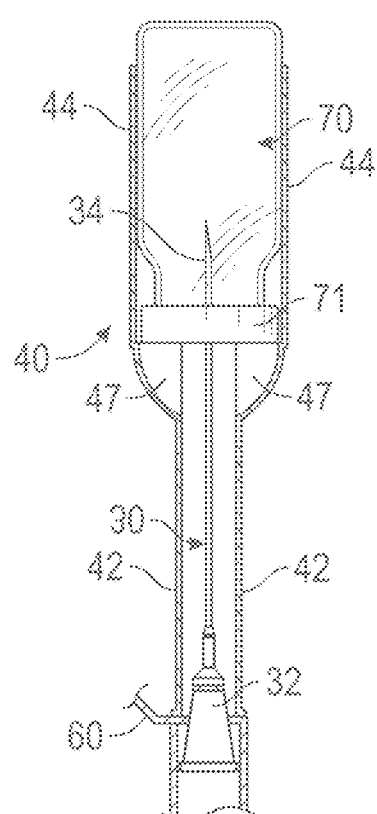
FIG. 8B shows a cross sectional view of the embodiment of the guiding element illustrated in FIG. 8A, albeit the vial has been inserted into a the guiding element barrel.

FIG. 8B shows a cross sectional view of the embodiment of guiding element 40 illustrated in FIG. 8A, albeit vial 70 has been inserted into guiding element barrel 44 and needle 30 has punctured the rubber septum of cap 71 and is being secured or otherwise engaged by guiding element barrel 44 in order to allow a user to draw medication from vial 70. In one or more embodiments, such configuration may be used to secure vial 70 and needle 30 below the medication level and reduce or eliminate the need for fine motor skills or other skills while administering medication under various working conditions, including adverse working conditions. As shown in FIG. 8B, the at least three wings 47 may be configured to contact cap 71 of vial 70 and control the depth at which needle 30 may access vial 70. In one or more embodiments, being configured with at least three wings 47 may aid in stabilizing the position of vial 70 while it is secured in the guiding element barrel 44. In one or more embodiments, guiding element barrel 44 may be configured such that it applies force on, grips, contracts, secures, or otherwise engages vial 70. In one or more embodiments, guiding element barrel 44 may be configured such that it positions or guides needle 30 into substantially the center of cap 71, thereby reducing the risk of bending, blunting, breaking or otherwise damaging needle 30. In one or more embodiments, once a user extracts medication from vial 70, the user may simply remove the guiding element 40 (which may be securing vial 70), expose needle 30 and inject the patient. Such configuration eliminates the step of requiring the end-user to attach needle 30 to syringe 20 after using guiding element 40 to extract the medication from vial 70 (because needle 30, in one or more embodiments, may already be attached to syringe 20 prior to accessing vial 70).

Figure 9:
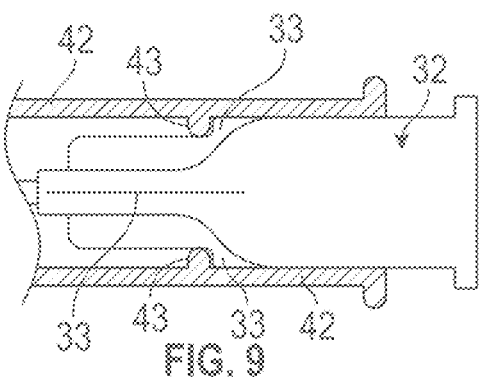
FIG. 9 shows a cross sectional view of one embodiment of aspects of a guiding element shaft.

FIG. 9 shows a cross sectional view of one embodiment of aspects of guiding element shaft 42, along with a side view of one embodiment of hub 32 of needle 30. In one or more embodiments, needle 30 may be housed within guiding element 40 in a substantially temporary fixed position while vial 70 is inserted into guiding element 40. In one or more embodiment, such an arrangement may allow a user to quickly and accurately insert needle 30 in the center of the vial 70 when vial 70 is inserted into guiding element 40. In one or more embodiments, guiding element 40 and needle 30 may be configured in various ways to accomplish the desired quickness and accuracy. For example, as shown in FIG. 9, in one or more embodiments, hub 32 may include wings 33 which may aid guiding element 40 in being operably connected to needle 30. In one or more embodiments, wings 33 may engage the inner wall of some aspect of guiding element 40 (such as guiding element shaft 42) and apply force on or engage said inner wall, thereby securing needle 30 in a substantially temporary fix, position within guiding element 40. As shown in FIG. 9, in one or more embodiments, the inner wall of guiding element shaft 42 may include a protrusion 43 which may be positioned on or circumference the inner wall, which when engaged by wings 33, may limit the distance needle 30 may travel into guiding element shaft 42.

FIGS. 10A-10F show various views of one embodiment of volume limiter 50.

Figure 10A:
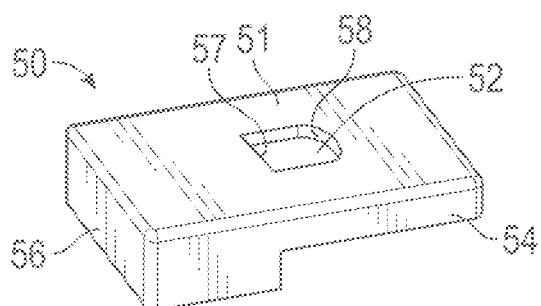
FIG. 10A shows a top perspective view of one embodiment of a volume limiter.

FIG. 10A shows a top perspective view of one embodiment of volume limiter 50. In one or more embodiments, medication delivery device 10 may provide a means for limiting the amount of medication that can be administered to a patient. For example, in one or more embodiments, volume limiter 50 may be configured to operably connect to syringe 20 and limit the amount of medication syringe 20 can draw from vial 70, thereby limiting the amount of medication that can be administered to a patient and prevent overdosing and ensure the correct dosage is administered. In one or more embodiments, as shown in FIG. 10A, volume limiter 50 may include a top surface 51, an opening 52 through which plunger 25 may be inserted, a bottom surface 53 (not shown in FIG. 10A), a first bottom ledge 54, a second bottom ledge 55 (not shown in FIG. 10A), and a first flange housing element 56. In one or more embodiments, as shown in FIG. 10A, opening 52 may include a first surface 57 (which may assume the contour of engagement section 26 of plunger 25) and a second surface 58 (which may assume the contour of a surface of plunger 25 alternate to engagement section 26 of plunger 25 discussed below). As shown in FIG. 10A, first surface 57 may be configured to be flat in order to conform to a notched or rebated engagement section 26. As shown in FIG. 10A, second surface 58 may be configured to be rounded.

Figure 10B:
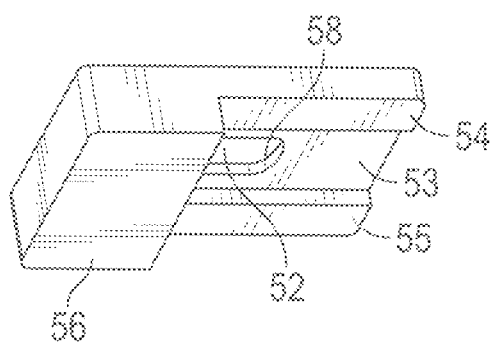
FIG. 10B shows a bottom perspective view of the embodiment of the volume limiter illustrated in FIG. 10A.

FIG. 10B shows a bottom perspective view of the embodiment of volume limber 50 illustrated in FIG. 10A.

Figure 10C:
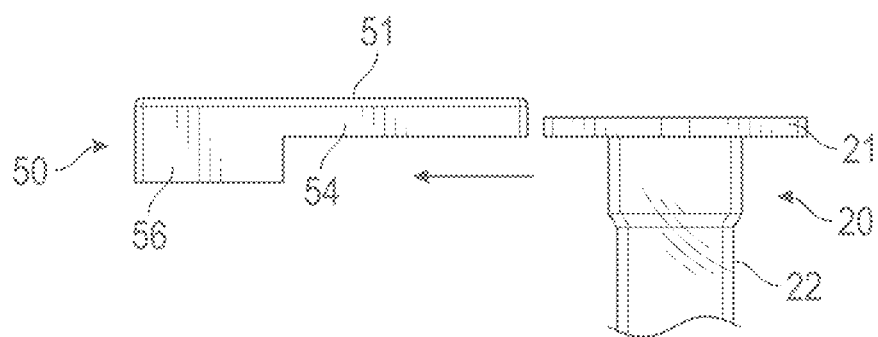
FIG. 10C shows a side view of the embodiment of the volume limiter illustrated in FIG. 10A, as well as an approaching syringe.

FIG. 10C shows a side view of the embodiment of volume limiter 50 illustrated in FIG. IDA, as well as an approaching embodiment of syringe 20. In one or more embodiments, first bottom ledge 54 and second bottom ledge 55 may be configured to allow flange 21 of syringe 20 to slide in between the two ledges and be secured by the same. In one or more embodiments, first flange housing element 56 may be configured to allow flange 21 of syringe 20 to slide into and be secured by it. Although not shown in FIG. 10C, in one or more embodiments, volume limiter 50 may be configured with various protrusions, ridges, indentations, or other configurations or materials, or combinations thereof, which may aid in securing syringe 20 to volume limiter 50. In one or more embodiments, the securement of syringe 20 to volume limiter 50 may be temporary, permanent, releasable, adjustable, resilient or otherwise engaged or any combination thereof.

Figure 10D:
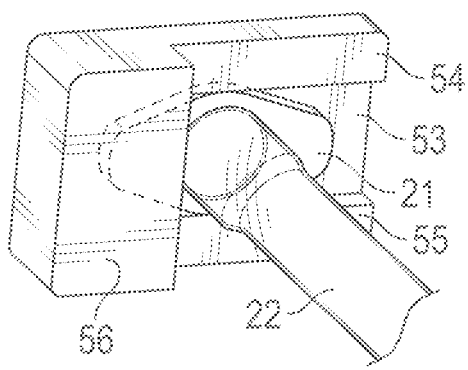
FIG. 10D shows a bottom perspective view of the embodiment of the volume limiter illustrated in FIG. 10A, wherein the flange of the syringe has been inserted into the volume limiter.

FIG. 10D shows a bottom perspective view of the embodiment of volume limiter 50 illustrated in FIG. 10A, wherein flange 21 of syringe 20 has been inserted in between first bottom ledge 54 and second bottom ledge 55 and positioned into first flange housing element 56.

Figure 10E:
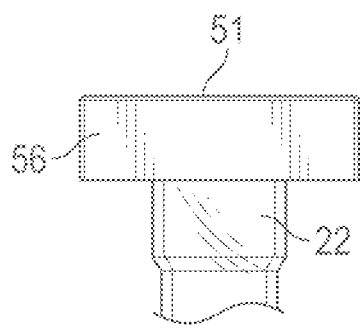
FIG. 10E shows a back view of the configuration of FIG. 10D.

FIG. 10E shows a back view of the configuration of FIG. 10D, wherein flange 21 of syringe 20 has been inserted in between first bottom ledge 54 and second bottom ledge 55 and positioned into first flange housing element 56.

Figure 10F:
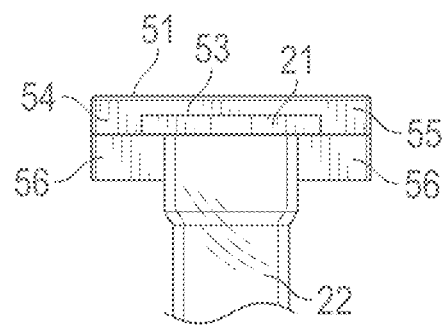
FIG. 10F shows a front view of the configuration of FIG. 10D.

FIG. 10F shows a front view of the configuration of FIG. 10D, wherein flange 21 of syringe 20 has been inserted in between first bottom ledge 54 and second bottom ledge 55 and positioned into first flange housing element 56.

Figure 11A:
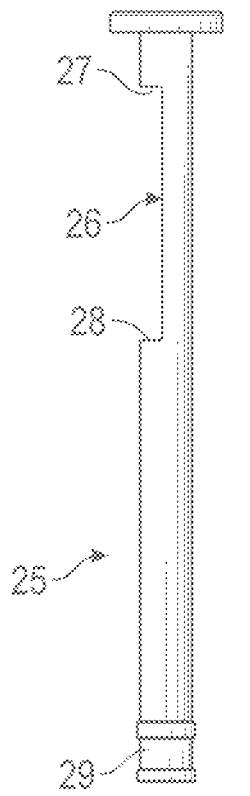
FIG. 11A shows a side view of one embodiment of a plunger.

FIG. 11A shows a side view of one embodiment of plunger 25. As shown in FIG. 11A, plunger 25 may include an engagement section 26 for limiting the distance the plunger can travel within the syringe barrel to prevent overdosing and ensuring the correct dosage is administered. As shown in FIG. 11A, engagement section 26 may be notched or rebated and include a first end 27 and a second end 28.

Figure 11B:
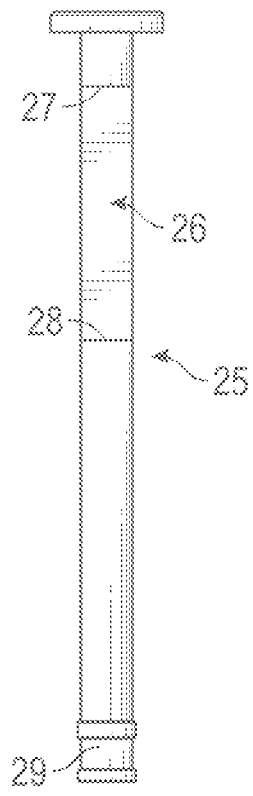
FIG. 11B shows a front view of the embodiment of the plunger illustrated in FIG. 11A.

FIG. 11B shows a front view of the embodiment of plunger 25 illustrated in FIG. 11A.

FIGS. 12A-12H show various views of the embodiment of plunger 25 illustrated in FIG. 11A being engaged with the embodiment of volume limiter 50 illustrated in FIG. 10A.

Figure 12A:
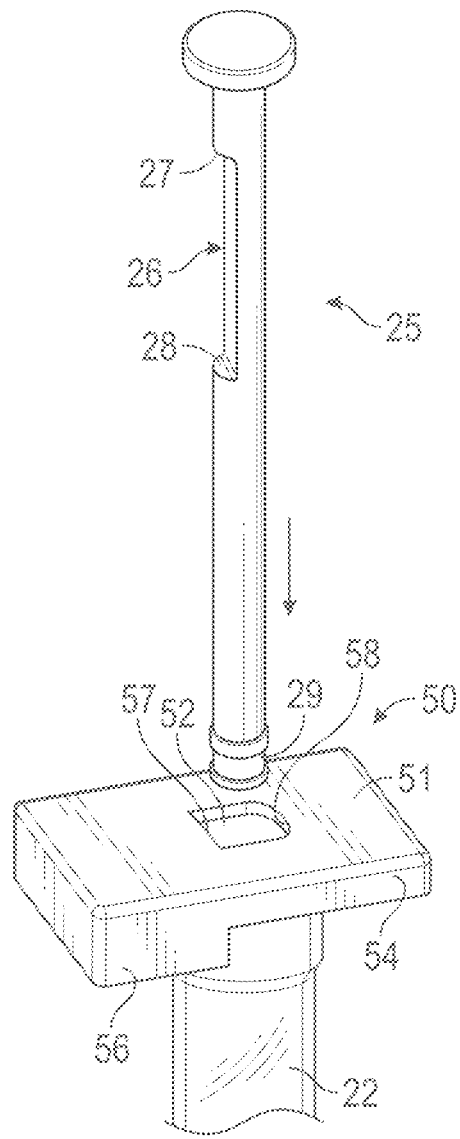
FIG. 12A shows a perspective view of the embodiment of the plunger illustrated in FIG. 11 approaching the embodiment of the volume limiter illustrated in FIG. 10A.

FIG. 12A shows a perspective view of the embodiment of plunger 25 illustrated in FIG. 11A approaching the embodiment of volume limiter 50 illustrated in FIG. 10A. As shown in FIG. 12A, one embodiment of syringe 20 may be operably connected to volume limiter 50, such as the volume limber 50 illustrated and described in relation to FIGS. 10C-10F.

Figure 12B:
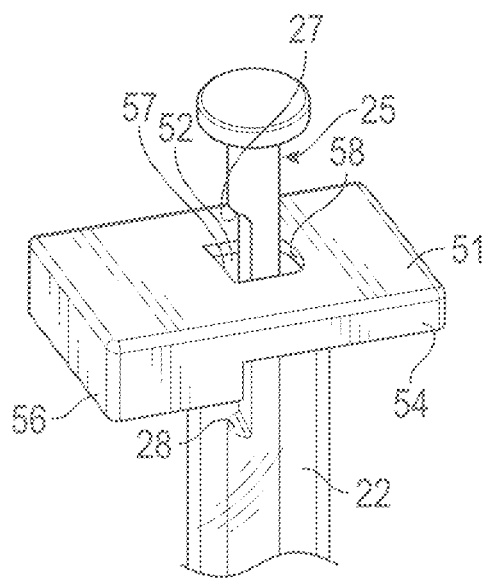
FIG. 12B shows a perspective view of the embodiment of the plunger illustrated in FIG. 11A inserted through an opening of the embodiment of the volume limiter illustrated in FIG. 10A.

FIG. 12B shows a perspective view of the embodiment of plunger 25 illustrated in FIG. 11A inserted through opening 52 of the embodiment of volume limiter 50 illustrated in FIG. 10A. As shown in FIG. 12R, plunger 25 may be positioned such that engagement section 26 is proximal to first surface 57 and that first end 27 is located on one side of volume limiter 50 and second end 28 located on another side of volume limiter 50.

Figure 12C:
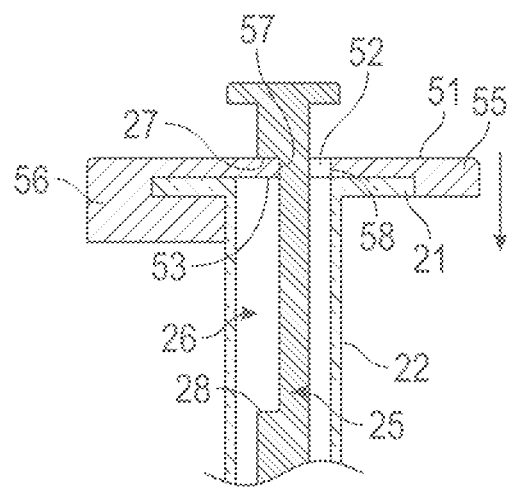
FIG. 12C shows a sectional view of the embodiment of the plunger illustrated in FIG. 11A inserted through the opening of the embodiment of the volume limiter illustrated in FIG. 10A.

FIG. 12C shows a sectional view of the embodiment of plunger 25 illustrated in FIG. 11A inserted through opening 52 of the embodiment of volume limiter 50 illustrated in FIG. 10A, wherein first surface 57 is engaging engagement section 26. As shown in FIG. 12C, in one or more embodiments, plunger 25 may be configured such that once plunger 25 is inserted through opening 52, plunger 25 may travel within syringe barrel 22 until first end 27 engages the top surface 51 of volume limber 50 or until plunger stopper 29 hits the bottom of syringe barrel 22. In one or more embodiments, once first end 27 of plunger 25 engages the top surface 51 of volume limiter 50 or plunger stopper 29 hits the bottom of syringe barrel 22, a user may be prevented from expelling substances (including liquid and air) from syringe 20 in that particular depression. Such configuration may at least be one way medication delivery device 10 may provide for limiting the amount of medication that can be injected into a patient and for limiting the amount of air a user may force into vial 70.

Figure 12D:
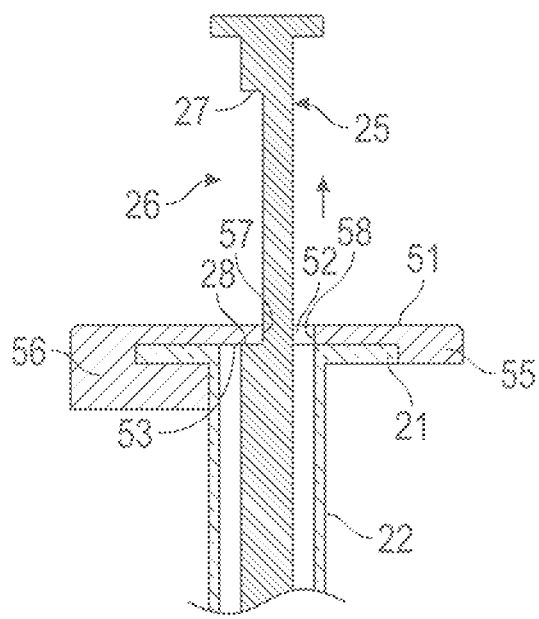
FIG. 12D shows a sectional view of the embodiment of the plunger illustrated in FIG. 11A inserted through the opening of the embodiment of the volume limiter illustrated in FIG. 10A, albeit that the plunger is situated in a different position in comparison with the position of the plunger as shown in FIG. 12C.

FIG. 12D shows a sectional view of the embodiment of plunger 25 illustrated in FIG. 11A inserted through opening 52 of the embodiment of volume limiter 50 illustrated in FIG. 10A, albeit that plunger 25 is situated in a different position in comparison with the position of plunger 25 as shown in FIG. 12C. As shown in FIG. 12D, in one or more embodiments, plunger 25 may be configured such that plunger 25 may travel within syringe barrel 22 until second end 28 engages the bottom surface 53 of volume limiter 50. Such configuration may be at least one way medication delivery device 10 may provide for limiting the amount of medication that can be drawn into syringe barrel 22 from vial 70 and thereby limiting the amount of medication that can be injected into a patient and preventing overdosing and ensure the correct dosage is administered.

Figure 12E:
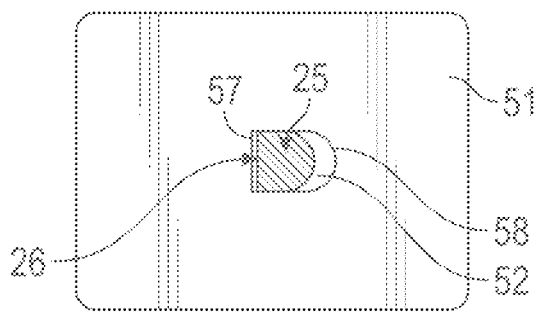
FIG. 12E shows a top view of a sectional view of the embodiment of the plunger illustrated in FIG. 11A inserted through the opening of the embodiment of the volume limiter illustrated in FIG. 10A.

FIG. 12E shows a top view of a sectional view of the embodiment of plunger 25 illustrated in FIG. 11A inserted through opening 52 of the embodiment of volume limiter 50 illustrated in FIG. 10A, wherein first surface 57 is engaging engagement section 26. In one or more embodiments, first surface 57 may engage engagement section 26 as plunger 25 travels within syringe 20.

FIG. 12F shows a perspective view of the embodiment of plunger 25 illustrated in FIG. 11A inserted through opening 52 and twisted to disengage volume limiter 50 from plunger 25 and allow plunger 25 to travel further to check for "flash" or for other reasons. As shown in FIG. 12F, plunger 25 may be twisted such that engagement section 26 does not catch on first surface 27. Such configuration may provide a means for disengaging volume limiter 50 from plunger 25 to allow plunger to travel further. In one or more embodiments, plunger 25 may be twisted to about 180 degrees to disengage volume limiter 50 from plunger 25 and allow plunger 25 to travel further. In one or more embodiments, alternative or additional means may be provided for disengaging volume limiter 50 from plunger 25 or some other aspect of medication delivery device 10 to allow plunger to travel further. For example, although not shown in FIG. 12F, in one or more embodiments, volume limiter 50 may be designed to allow a user to shift or otherwise reposition volume limiter 50 in order to disengage it from plunger 25 or some other component of medication delivery device 10 (such as shifting first surface 57 so that it disengages engagement section 26 of plunger 25), thereby allowing plunger 25 to travel further. Such configuration(s) may be in addition to or alternative to being able to twist plunger 25 to disengage the volume limiter 50.

FIG. 12G shows a top view of a sectional view of the embodiment of plunger 25 illustrated in FIG. 11A inserted through opening 52 and twisted (as shown in FIG. 12F) such that engagement section 26 is proximal to second surface 58, thereby disengaging volume limiter 50 from plunger 25.

FIG. 12H shows a sectional view of the embodiment of plunger 25 illustrated in FIG. 11A inserted through opening 52 and twisted (as shown in FIGS. 12F and 12G). As shown in FIG. 12H, in one or more embodiments, once plunger 25 may be twisted so that engagement section 26 is not proximal to first surface 57, plunger 25 may travel within syringe barrel 22 at a greater distance because engagement section 26 does not catch on bottom surface 53. In one or more embodiments, such an arrangement may allow a user, who has already inserted needle 30 into a patient, to draw back and check for blood or extract substances from a patient. Although not shown in FIG. 12H, in one or more embodiments, after twisting plunger 25 or otherwise disengaging volume limiter 50 from engagement section 26, plunger 25 may be removed through opening 52 and separated from medication delivery device 10. Although not shown in FIG. 12H, in one or more embodiments, twisting plunger 25 may cause volume limiter 50 to shift (such as substantially perpendicularly to plunger 25) to aid in allowing plunger 35 to travel further.

FIGS. 13A-13B show various views of one embodiment of volume limiter 50 including a retention member 80.

FIG. 13A shows a bottom perspective view of the configuration illustrated in FIG. 10D, albeit volume limiter 50 shown in FIG. 13A includes a retention member 80. In one or more embodiments, medication delivery device 10 may provide a means for at least temporarily and resiliently securing the operable connection of volume limiter 50 with syringe 20. For example, in one or more embodiments, retention member 80 may be a rubber band or some other material that may be stretched around various components of medication delivery device 10 in order to temporarily and resiliently secure volume limiter 50 with syringe 20. As shown in FIG. 13A, in one or more embodiments, retention member 80 may be positioned around one side of syringe 20 and the opposite corners of first flange housing element 56 and top surface 51 such that syringe 20 is temporarily and resiliently placed in a fixed position relative to volume limiter 50. In one or more embodiments, as plunger 25 is twisted or otherwise moved relative to volume limiter 50, volume limiter 50 may resiliently shift positions or slide along flange 21. In one or more embodiments, medication delivery device 10 may provide a means for automatically engaging volume limiter 50 for limiting the amount of medication that can be drawn from vial 70, thereby limiting the amount of medication that can be administered to a patient. For example, in one or more embodiments, retention member 80 may enable volume limiter 50 to automatically engage plunger 25 when plunger 25 is depressed through opening 52. In one or more embodiments, as plunger 25 is inserted and depressed through opening 52 (such as shown in FIGS. 12A-12C) with engagement section 26 aligned with the first surface 57 of opening 52, retention member 80 may enable volume limiter 50 to automatically adjust to the contour of and apply force on the surface of engagement section 26. In one or more embodiments, once second end 28 travels through opening 52 and past bottom surface 53, retention member 80 may enable volume limiter 50 to automatically snap against and apply force on engagement section 26, and thereby limit the distance plunger 25 may travel to the distance between first end 27 and second end 28 (as shown in FIGS. 12C and 12D). Such means for automatically engaging volume limiter 50 may, in one or more embodiments, allow plunger 25 to be provided to a user in a drawn position with second end 28 positioned against or proximal to bottom surface 53 ready for the user to (1) insert an attached needle 30 into vial 70 with the aid of guiding element 40, (2) depress plunger 25 and force air into vial 70, and (3) let pressure force plunger 25 back and fill syringe 20 with medication from vial 70 up to the point at which second end 28 engages bottom surface 53. Such configuration may limit the amount of medication that can be drawn from vial 70 and thereby limit the amount of medication that can be administered to a patient and prevent overdosing and ensure the correct dosage is administered.

FIG. 13B shows a top perspective view of the embodiment of volume limiter 50 illustrated in FIG. 13A including a retention member 80.

FIGS. 14-26E show views of various embodiments of volume limiter 50, plunger 25 and syringe 20 that may, in one or more embodiments, be mixed and matched and substituted with other embodiments of volume limiter 50, plunger 25 and syringe 20 contained herein.

Figure 14:
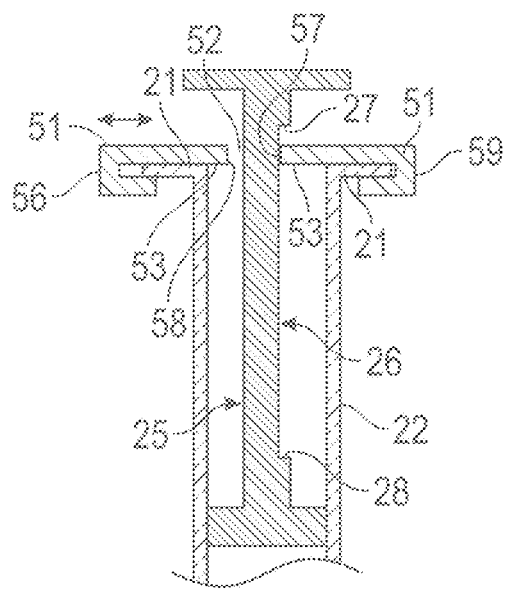
FIG. 14 shows a cross sectional view of another embodiment of a volume limiter.

FIG. 14 shows a cross sectional view of one embodiment of volume limiter 50 which may be operably connected to syringe 20 such that it may not be removed. As shown in FIG. 14, volume limiter 50 may include first flange housing element 56 and a second flange housing element 59, as well as top surface 51, opening 52 (which may include first surface 57 and second surface 58) and bottom surface 53. In one or more embodiments, first flange housing element 56 and second flange housing element 59 engage at least aspects of flange 21 such that volume limiter 50 may not be removed from syringe 20. For example, second flange housing element 59 may be configured similar to the first flange housing element 56 illustrated in FIGS. 10A through 10F, albeit second flange housing element 59 may be located on the opposite side of volume limiter 50. In one or more embodiments, first surface 57 of opening 52 may be configured so that first surface 57 engages engagement section 26 of plunger 25 in order to limit the distance plunger 25 may travel between second end 28 and first end 27, and thereby limiting the amount of medication that can be drawn from vial 70 and thereby limiting the amount of medication that can be administered to a patient and preventing overdosing and ensure correct dosages. In one or more embodiments, volume limiter 50 may be manually repositioned, shifted or otherwise moved or operated (such as substantially perpendicularly in relation to plunger 25) by a user in order to move first surface 57 away from engagement section 26 and disengage volume limiter 50 from plunger 25. Such configuration may be one embodiment of a means for disengaging volume limiter 50 from plunger 25 to allow plunger 25 to travel further and check for blood or other factors.

Figure 15:
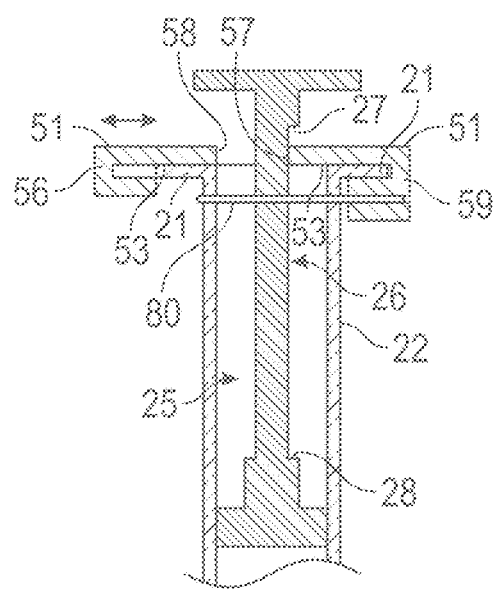
FIG. 15 shows a cross sectional view of another embodiment of a volume limiter.

FIG. 15 shows a cross sectional view of one embodiment of volume limiter 50 that includes retention member 80 for automatically engaging volume limiter 50 for limiting the amount of medication that can be drawn from vial 70, thereby limiting the amount of medication that can be administered to a patient and preventing overdosing and ensuring correct dosages. As shown in FIG. 15, volume limiter 50 may include top surface 51, opening 52 (which may include first surface 57 and second surface 58), bottom surface 53, first flange housing element 56 and second flange housing element 59. In one or more embodiments, second flange housing element 59 may be configured to retain at least one aspect of retention member 80 while another aspect of retention member 80 may be secured around an oppositely situated side of syringe 20 such that when second end 28 of plunger 25 is depressed through opening 52, with engagement section 26 aligned with first surface 57 of opening 52, retention member 80 may enable volume limiter 50 to automatically adjust to the contour of engagement section 26 and automatically snap against and apply force on engagement section 26 and thereby limit the distance plunger 25 may travel to the distance between first end 27 and second end 28. Such means for automatically engaging volume limiter 50 may, in one or more embodiments, allow plunger 25 to be provided to a user in a drawn position with second end 28 positioned against bottom surface 53 ready for the user to (1) insert an attached needle 30 into vial 70 with the aid of guiding element 40, (2) depress plunger 25 and force air into vial 70, and (3) let pressure force plunger 25 back and fill syringe 20 with medication from vial 70 up to the point at which second end 28 engages bottom surface 53. Such configuration may limit the amount of medication that can be drawn from vial 70 and thereby limit the amount of medication that can be administered to a patient. Such configuration may provide means for at least temporarily and resiliently securing the operable connection of volume limiter 50 with syringe 20. In one or more embodiments, volume limiter 50 may be manually repositioned, shifted or otherwise moved (such as substantially perpendicularly in relation to plunger 25) by a user in order to move first surface 57 away from engagement section 26 and disengage volume limiter 50 from plunger 25. Such configuration may be one embodiment of a means for disengaging volume limiter 50 from plunger 25 to allow plunger 25 to travel further and check for blood or other factors.

Figure 16A:
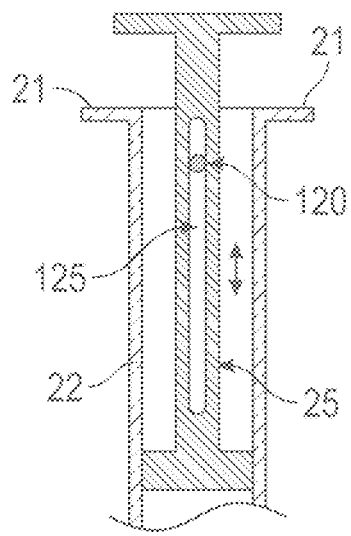
FIG. 16A shows a cross sectional view of another embodiment of a volume limiter.

FIG. 16A shows a cross sectional view of one embodiment of volume limiter 50 configured as a pin 120 which pin 120 corresponds with a channel 125 manufactured into plunger 25. In one or more embodiments, instead of limiting the amount of medication delivery device 10 may be drawn into syringe 20 by use of plunger 25 with an engagement section 26, the embodiment shown in FIG. 16A uses a pin-channel combination to limit the amount of medication that can be drawn from vial 70, thereby limiting the amount of medication that can be administered to a patient and preventing overdosing and ensuring correct dosages. In one or more embodiment, a user may pull pin 120 out and disengage volume limiter 50 from plunger 25 to allow plunger 25 to travel further. In one or more embodiments, although not shown on FIG. 16A, the location on syringe 20 wherein pin 120 may be inserted may vary, thus providing an adjustable volume limiter 50 to allow various dosages to be administered.

Figure 16B:
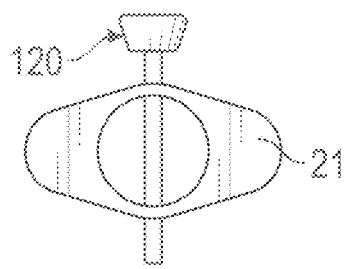
FIG. 16B shows a top view of one embodiment of a flange with a pin inserted through a syringe as shown in FIG. 16A.

FIG. 16B shows a top view of one embodiment of flange 21 with pin 120 inserted through syringe 20 as shown in FIG. 16A (plunger 25 is not shown in FIG. 16B).

Figure 17A:
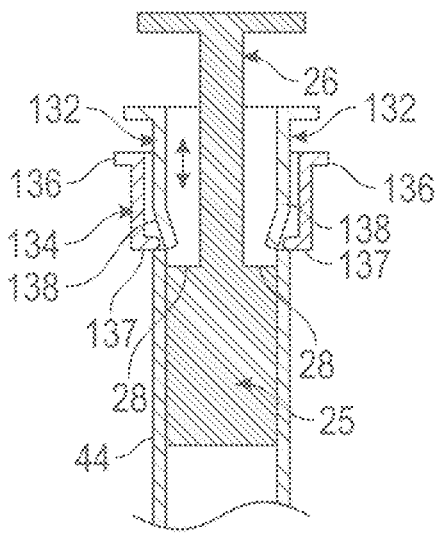
FIG. 17A shows a cross sectional view of another embodiment of a volume limiter.

FIG. 17A shows a cross sectional view of one embodiment of volume limiter 50 which may include an inner collar 132 and an outer collar 134 which interact to provide means for automatically engaging volume limiter 50 for limiting the amount of medication that can be drawn from vial 70, thereby limiting the amount of medication that can be administered to a patient and preventing overdosing and ensuring correct dosages. In one or more embodiments, outer collar 134 may include a first end 136 and a second end 137. As shown in FIG. 17A, in one or more embodiments, outer collar 134 may assume an elongated "S" shape wherein second end 137 is operably connected to the top portion of syringe 20 and protrudes inwardly towards plunger 25. In one or more embodiments, inner collar 132 may include a flexible portion 138. In one or more embodiments, inner collar 132 may assume a profile substantially similar to the circumference of syringe 20 and slideably fit within the circumference of outer collar 134. In one or more embodiments, flexible portion 138 may slide over second end 137 and protrude into syringe 20 and engage second end 28 of engagement section 26 when plunger 25 may be drawn back in order to prevent plunger 25 from travelling back any further. Such configuration may provide means for automatically engaging volume limiter 50 for limiting the amount of medication that can be drawn from vial 70, thereby limiting the amount of medication that can be administered to a patient and preventing overdosing and ensuring correct dosages. In one or more embodiments, inner collar 132 may be designed to slide parallel relative to plunger 25 as a user pulls on inner collar 132. In one or more embodiments, as inner collar 132 slides away from needle 30, flexible portion 138 may be positioned above second end 137, allowing flexible portion 138 to flex toward outer collar 134 and out of the path of plunger 25, thereby providing means for disengaging volume limiter 50 from plunger 25 to allow plunger 25 to travel further.

Figure 17B:
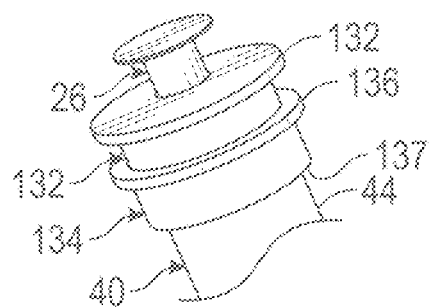
FIG. 17B shows a perspective view of the embodiment of the volume limiter illustrated in FIG. 17A.

FIG. 17B shows a perspective view of the embodiment of volume limiter 50 illustrated in FIG. 17A.

Figure 18A:
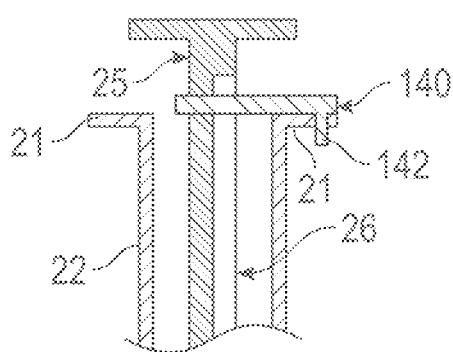
FIG. 18A shows a cross sectional view of another embodiment of a volume limiter.

FIG. 18A shows a cross sectional view of one embodiment of volume limiter 50 including a swivelable plate 140 which engages engagement section 26 of plunger 25 to provide means for limiting the amount of medication that can be drawn from vial 70, thereby limiting the amount of medication that can be administered to a patient and preventing overdosing and ensuring correct dosages. In one or more embodiments, a user may pivot swivelable plate 140 around a pivot 142 in order to engage engagement section 26. Although not shown in FIG. 18A, in one or more embodiments, engagement section 26 may include first end 27 and second end 28. In one or more embodiments, when engagement section 26 is aligned with swivelable plate 140, swivelable plate 140 may limit the distance plunger 25 may travel to the distance between first end 27 and second end 28, thereby limiting the amount of medication that can be drawn from vial 70, thereby limiting the amount of medication that can be administered to a patient. In one or more embodiments, whenever a user desires to disengage volume limiter 50, the user may simply move the swivelable plate 140 and disengage it from the engagement section 26 of plunger 25. Such configuration may provide means for disengaging volume limiter 50 from plunger 25 to allow plunger 25 to travel further.

Figure 18B:
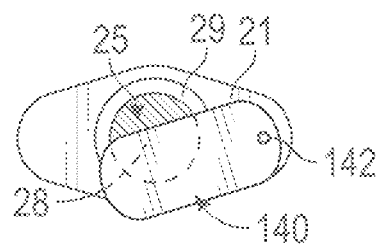
FIG. 18B shows a top view of the embodiment of the volume limiter as illustrated in FIG. 18A.

FIG. 18B shows a top view of the embodiment of volume limiter 50 as illustrated in FIG. 18A including a swivelable plate 140 which engages engagement section 26 of plunger 25.

Figure 19A:
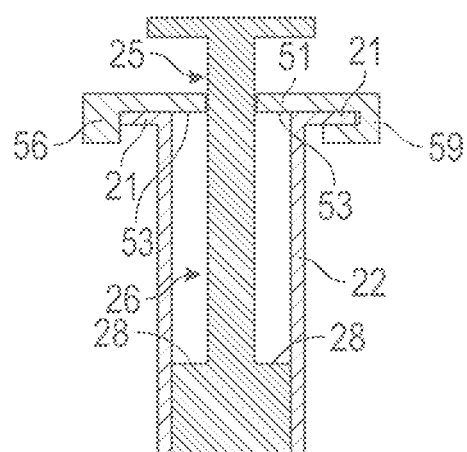
FIG. 19A shows a cross sectional view of another embodiment of a volume limiter.

FIG. 19A shows a cross sectional view of one embodiment of volume limiter 50 that may be capable of being twisted on and off of syringe 20 and engaging and disengaging volume limiter 50 from plunger 25 to prevent and allow plunger 25 to travel. As shown in FIG. 19A, volume limiter 50 may include top surface 51, opening 52 (which may include first surface 57 and second surface 58), bottom surface 53, first flange housing element 56 and second flange housing element 59. In one or more embodiments, first flange housing element 56 and second flange housing element 59 may each engage portions of opposing ends of flange 21. To engage first flange housing element 56 and second flange housing element 59, in one or more embodiments, a user may simply twist volume limiter 50 on flange 21 in one direction. To disengage first flange housing element 56 and second flange housing element 59, in one or more embodiments, a user may simply twist volume limiter 50 off flange 21 in an opposing direction. In one or more embodiments, when engaging flange 21, first flange housing element 56 and second flange housing element 59 may prevent plunger 25 from travelling any further when drawn back by engaging second end 28.

Figure 19B:
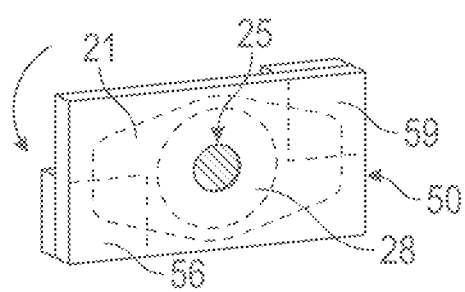
FIG. 19B shows a top perspective view of the embodiment of the volume limiter illustrated in FIG. 19A.

FIG. 19B shows a top perspective view of the embodiment of volume limiter 50 illustrated in FIG. 19A. In one or more embodiment, first flange housing element 56 and second flange housing element 59 may engage flange 21 by twisting around flange 21 in a clockwise rotation (or in a counterclockwise rotation in another embodiment) and first flange housing element 56 and second flange housing element 59 may disengage flange 21 by twisting around flange 21 in the opposite rotation.

Figure 20:
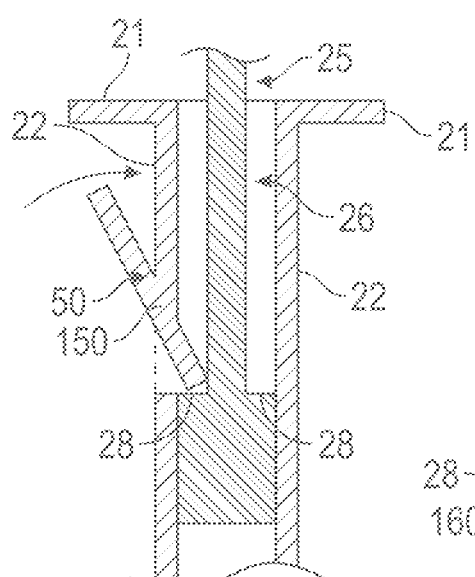
FIG. 20 shows a cross sectional view of one embodiment of a syringe including one embodiment of a volume limiter built into a syringe barrel.

FIG. 20 shows a cross sectional view of one embodiment of syringe 20 including one embodiment of volume limiter 50 built into syringe barrel 22. As shown in FIG. 20, one aspect of syringe barrel 22 may include a flexible member 150 which may engage second end 28 when plunger 25 is pulled back into drawn position to limit the distance plunger 25 may be pulled back and to provide means for limiting the amount of medication that can be drawn from vial 70. Such configuration may provide means for automatically engaging volume limiter 50 for limiting the amount of medication that can be drawn from vial 70, thereby limiting the amount of medication that can be administered to a patient and preventing overdosing and ensuring correct dosages. In one or more embodiments, flexible member 150 may resiliently bend upon manipulation. In one or more embodiments, a user may manipulate flexible member 150 such that its position limits the travel distance of plunger 25 upon interaction with second end 28 or, alternatively or additionally, does not limit the travel distance of plunger 25. Such configuration may provide means for disengaging volume limiter 50 from plunger to allow plunger 25 to travel further. In one or more embodiments, flexible member 150 may be provided in a position set to limit the travel distance of plunger 25 upon interaction with second end 28 or in a non-limiting position.

Figure 21A:
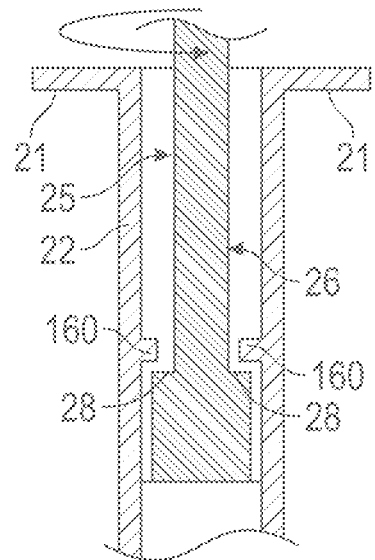
FIG. 21A shows a cross sectional view of another embodiment of a syringe including one embodiment of a volume limiter built into a syringe barrel.

FIG. 21A shows a cross sectional view of one embodiment of syringe 20 including one embodiment of volume limiter 50 built into syringe barrel 22, alternative to the configuration shown in FIG. 20. As shown in FIG. 21A, syringe barrel 22 may include volume limiter 50 built into syringe barrel 22 as protrusions 160 which limit the distance plunger 25 may travel, thereby limiting the amount of medication that can be drawn from vial 70, thereby limiting the amount of medication that can be administered to a patient and preventing overdosing and ensuring correct dosages. In one or more embodiments, protrusions 160 may engage second end 28 as plunger 25 is drawn back and prevent plunger 25 from being able to be drawn back further. In one or more embodiments, plunger 25 may be cut such that a user may rotate plunger 25 to position second end 28 so that second end 28 clears protrusions 160, thereby allowing plunger to be drawn back further than when protrusions 160 engage second end 28. Such configuration may provide means for disengaging volume limiter 50 from plunger 25 or some other aspect of medication delivery device 10 to allow plunger 25 to travel further.

Figure 21B:
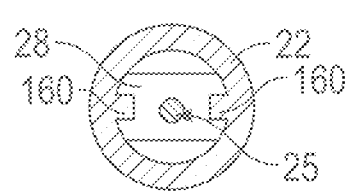
FIG. 21B shows a top view of the embodiment of the syringe illustrated in FIG. 21A.

FIG. 21B shows a top view of the embodiment of syringe 20 illustrated in FIG. 21A, wherein volume limiter 50 is engaging plunger 25 via protrusions 160.

Figure 21C:
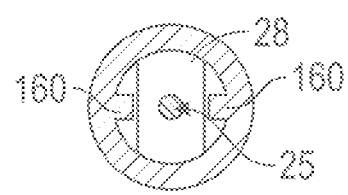
FIG. 21C shows a top view of the embodiment of the syringe illustrated in FIG. 21A, wherein the plunger has been rotated.

FIG. 21C shows a top view of the embodiment of syringe 20 illustrated in FIG. 21A, wherein plunger 25 has been rotated to disengage protrusions 160.

Figure 22A:
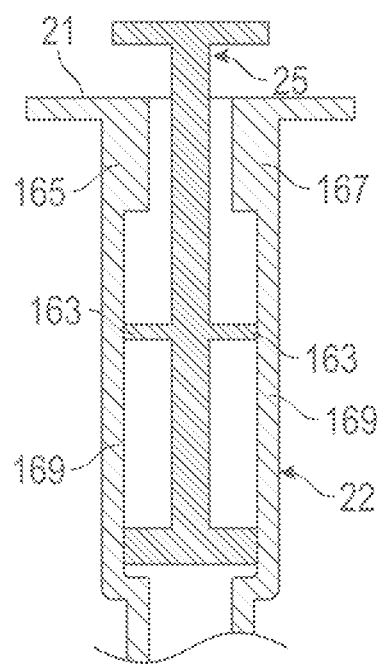
FIG. 22A shows a cross sectional view of one embodiment of a plunger including one embodiment of volume limiter built into the plunger.

FIG. 22A shows a cross sectional view of one embodiment of plunger 25 including one embodiment of volume limiter 50 built as protrusions 163 into plunger 25. Unlike the embodiment of disclosure illustrated in FIG. 21A where volume limiter's 50 protrusions 160 may be built into syringe barrel 22, the embodiment illustrated in FIG. 22A shows protrusions 163 built into plunger 25. In one or more embodiments, syringe barrel 22 may include a first wall section 165, a second wall section 167 and a third wall section 169. In one or more embodiments, first wall section 165 and second wall section 167 may be located proximal to flange 21 and may be thicker than third wall section 169, which third wall section 169 may be distal to flange 21. In one or more embodiments, first wall section 165 and second wall section 167 may be configured to engage protrusions 163 and limit the distance plunger 25 may travel back. Such configuration may be a means for limiting the amount of medication that can be drawn from vial 70, thereby limiting the amount of medication that can be administered to a patient and preventing overdosing and ensuring correct dosages.

Figure 22B:
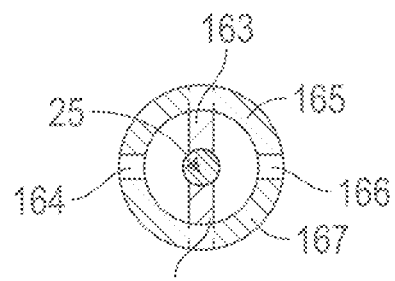
FIG. 22B shows a top view of the embodiments of the plunger illustrated in FIG. 22A.

FIG. 22B shows a top view of the embodiments of plunger 25 and syringe barrel 22 illustrated in FIG. 22A, wherein syringe barrel 22 is engaging protrusions 163. In one or more embodiments, syringe barrel 22 may include a first channel 164 and a second channel 166 wherein protrusions 163 may pass through in order to clear first wall section 165 and second wall section 167. In one or more embodiments, as shown in FIG. 22B, first channel 164 and second channel 166 may be located on opposite sides of syringe barrel 22. In one or more embodiments, as shown in FIG. 22B, first channel 164 may be situated between first wall section 165 and second wall section 167 on one side of syringe barrel 22 and second channel 166 may be situated between first wall section 165 and second wall section 167 on an alternate side of syringe barrel 22.

Figure 22C:
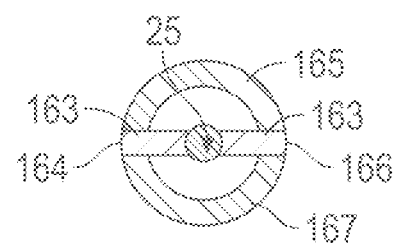
FIG. 22C shows a top view of the embodiments of the plunger illustrated in FIG. 22A, wherein the plunger has been rotated.

FIG. 22C shows a top view of the embodiments of plunger 25 and syringe barrel 22 illustrated in FIG. 22A, wherein plunger 25 has been rotated to disengage protrusions 163 from syringe barrel 22. In one or more embodiments, a user may rotate plunge 25 such that protrusions 163 clear first wall section 165 and second wall section 167 and such that one protrusion 163 may travel along first channel 164 and another protrusion 163 may travel along second channel 166, allowing plunger 25 to travel further back in comparison to when protrusions 163 may be engaged by first wall section 165 and second wall section 167. Such configuration may provide means for disengaging protrusions 163 from syringe barrel 22 to allow plunger 25 to travel further.

Figure 23:
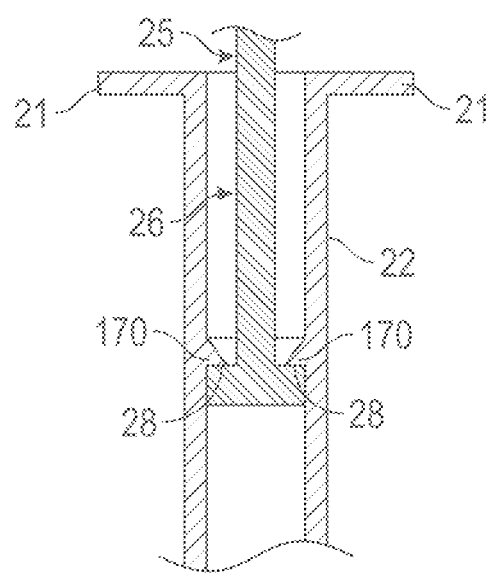
FIG. 23 shows a cross sectional view of one embodiment of a syringe including one embodiment of a volume limiter built into a syringe barrel.

FIG. 23 shows a cross sectional view of one embodiment of syringe 20 including one embodiment of volume limiter 50 built into syringe barrel 22, which configuration may be a permanent volume limiter 50 configuration. As shown in FIG. 23, syringe barrel 22 may include volume limiter 50 built into syringe barrel 22 as protrusion 170 for limiting the distance plunger 25 may travel by engaging second end 28, thereby limiting the amount of medication that can be drawn from vial 70, thereby limiting the amount of medication that can be administered to a patient and preventing overdosing and ensuring correct dosages.

Figure 24A:
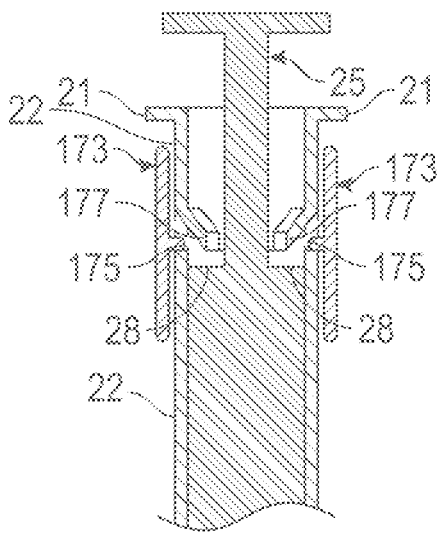
FIG. 24A shows a cross sectional view of one embodiment of a volume limiter and syringe including a syringe barrel.

FIG. 24A shows a cross sectional view of one embodiment of volume limiter 50 which may include a single collar 173 including at least one protrusion 175. In one or more embodiments, the at least one protrusion 175 may protrude from single collar 173 and may engage at least one flexible section 177 of syringe barrel 22. In one or more embodiments, a user may twist collar 173 around syringe barrel 22 such that the at least one protrusion 175 may engage the at least one flexible section 177 of syringe barrel 22 and engage second end 28 and prevent plunger 25 from traveling further back, thereby limiting the amount of medication that can be drawn from vial 70. Such configuration may provide means for automatically engaging volume limiter 50 for limiting the amount of medication that can be drawn from vial 70, thereby limiting the amount of medication that can be administered to a patient and preventing overdosing and ensuring correct dosages.

Figure 24B:
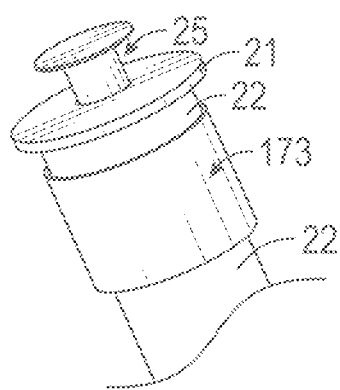
FIG. 24B shows a perspective view of the embodiment of the volume limiter illustrated in FIG. 24A.

FIG. 24B shows a perspective view of the embodiment of volume limiter 50 illustrated in FIG. 24A.

Figure 24C:
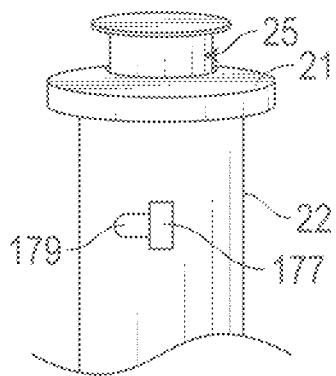
FIG. 24C shows a perspective view of the embodiment of the syringe barrel illustrated in FIG. 24A showing at least one flexible section and including a pocket.

FIG. 24C shows a perspective view of the embodiment of syringe barrel 22 illustrated in FIG. 24A showing at least one flexible section 177 and including a pocket 179 wherein at least one protrusion 175 may reside when disengaged from the at least one flexible section 177. In one or more embodiments, when the at least one flexible section 177 is disengaged plunger 25 may travel further back as compared to when the at least one flexible section 177 is engaged. Such configuration may provide means for disengaging volume limiter 50 from plunger 25 or some other aspect of medication delivery device 10 to allow plunger 25 to travel further.

Figure 25A:
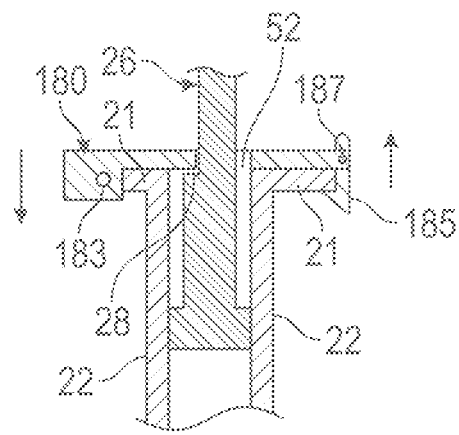
FIG. 25A shows a cross sectional view of one embodiment of a volume limiter configured as an articulable door.

FIG. 25A shows a cross sectional view of one embodiment of volume limiter 50 configured as an articulable door 180 which may pivot about pivot 183. In one or more embodiments, articulable door 180 may engage second end 28 and prevent plunger 25 from traveling further back, thereby limiting the amount of medication that can be drawn from vial 70, thereby limiting the amount of medication that can be administered to a patient and preventing overdosing and ensuring correct dosages. As shown in FIG. 25A, articulable door 180 may include a hook 185 which may pivot about pivot 187. In one or more embodiments, hook 185 may engage flange 21, and when so engaged, hook 185 may prevent articulable door 180 from articulating and may aid in securing articulable door 180 to flange 21. In one or more embodiments, pivot 183 may be operably configured to flange 21. In one or more embodiments, pivot 187 may be operably configured to articulable door 180.

Figure 25B:
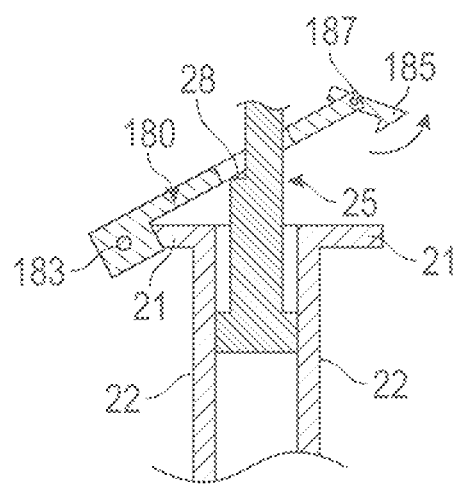
FIG. 25B shows a cross sectional view of the embodiment of the volume limiter illustrated in FIG. 25A, albeit the articulable door has been disengaged, from a flange.

FIG. 25B shows a cross sectional view of the embodiment of volume limiter 50 configured as articulable door 180 as illustrated in FIG. 25A, albeit articulable door 180 has been disengaged from flange 21. In one or more embodiments, a user may manipulate hook 185 and disengage it from flange 21, thereby allowing articulable door 180 to articulate about pivot 183, thereby allowing plunger 25 to travel further back as compared to when articulable door 180 is seemed to flange 21 and unable to articulate about pivot 183. Such configuration may provide means for disengaging volume limiter 50 from plunger 25 to allow plunger 25 to travel further.

Figure 26A:
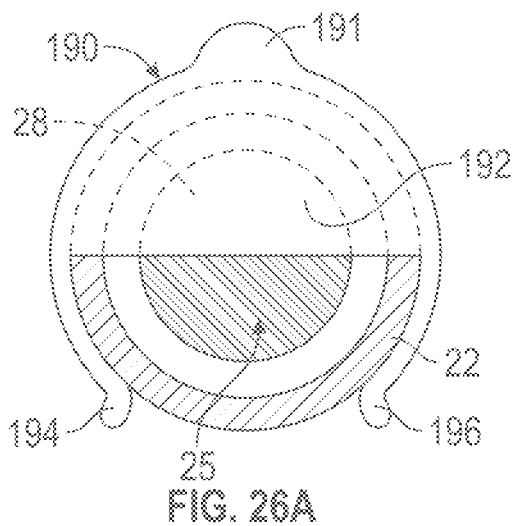
FIG. 26A shows a front view of one embodiment of a volume limiter configured as a detachable collar.

FIG. 26A shows a front view of one embodiment of volume limiter 50 configured as a detachable collar 190. In one or more embodiments, detachable collar 190 may be configured to be detachably secured to syringe barrel 22. In one or more embodiments, detachable collar 190 may include a wing member 192 designed to be inserted through the wall of syringe barrel 22 to engage second end 28 of plunger 25 and prevent plunger 25 from travelling further back, thereby limiting the amount of medication that can be drawn from vial 70. Such configuration may provide means for automatically engaging volume limiter 50 for limiting the amount of medication that can be drawn from vial 70, thereby limiting the amount of medication that can be administered to a patient and preventing overdosing over dosing and ensuring correct dosages. In one or more embodiments, detachable collar 190 may include a first arm member 194 and a second arm member 196, at least a portion of which may be situated to engage syringe barrel 22 and aid in retaining the operable connection of detachable collar 190 to syringe barrel 22. In one or more embodiments, detachable collar 190 may include a handle 191 to aid a user in grasping and detaching detachable collar 190 from syringe barrel 22, thereby allowing plunger 25 to travel past wing member 192. Such configuration may provide means for disengaging volume limiter 50 from plunger 25 or some other aspect of medication delivery device 10 to allow plunger 25 to travel further.

Figure 26B:
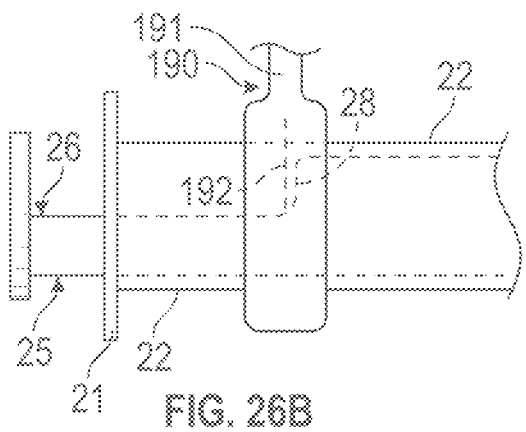
FIG. 26B shows a side view of the embodiment of the volume limiter illustrated in FIG. 26A.

FIG. 26B shows a side view of the embodiment of volume limiter 50 illustrated in FIG. 26A.

Figure 26C:
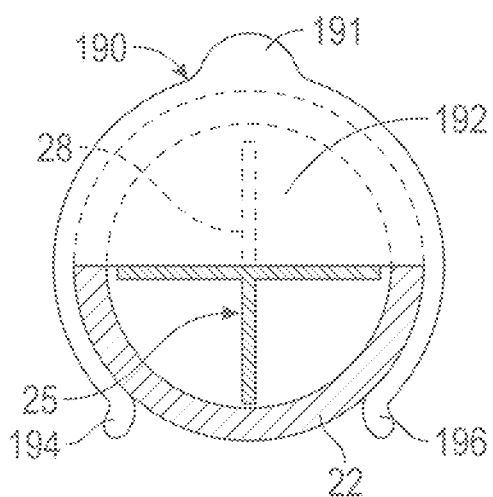
FIG. 26C shows a front view of the embodiment of the volume limiter as illustrated in FIG. 26A, albeit a plunger assumes a cruciform configuration.

FIG. 26C shows a front view of the embodiment of volume limiter 50 configured as a detachable collar 190 as illustrated in FIG. 26A, albeit plunger 25 assumes a cruciform configuration.

Figure 26D:
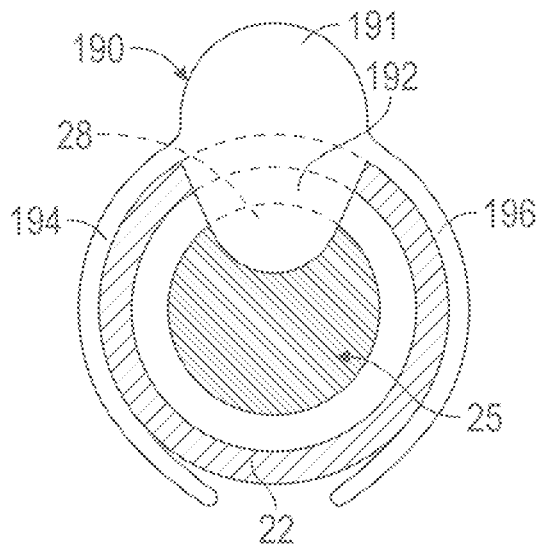
FIG. 26D shows a front view of the embodiment of a volume limiter similar to the embodiment of the volume limiter illustrated in FIG. 26A, albeit a wing member is smaller, a handle is larger and a first arm member and second arm member assume an alternative design.

FIG. 26D shows a front view of the embodiment of volume limiter 50 configured as a detachable collar 190 similar to the embodiment of volume limiter 50 illustrated in FIG. 26A, albeit wing member 192 is smaller and handle 191 is larger as compared to the embodiment of volume limiter 50 illustrated in FIG. 26A and albeit first arm member 194 and second arm member 196 assume an alternative design at their tips.

Figure 26E:
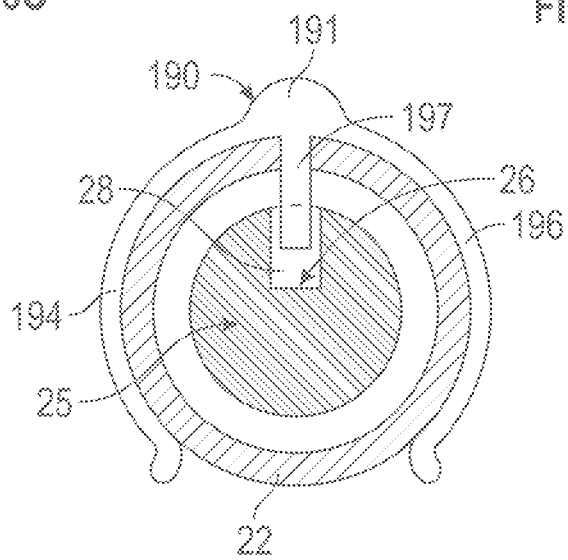
FIG. 26E shows a front view of the embodiment of a volume limiter similar to the embodiment of the volume limiter illustrated in FIG. 26A, albeit a wing member is replaced with a protrusion.

FIG. 26E shows a front view of the embodiment of volume limiter 50 configured as a detachable collar 190 similar to the embodiment of volume limiter 50 illustrated in FIG. 26A, albeit wing member 192 is replaced with a protrusion 197 designed to be inserted through the wall of syringe barrel 22 for engaging second end 28 of plunger 25 and preventing plunger 25 from travelling further back, thereby limiting the amount of medication that can be drawn from vial 70, thereby limiting the amount of medication that can be administered to a patient and preventing overdosing and ensuring correct dosages.

FIGS. 27A-35B show views of various embodiments of guiding element 40 that may, in one or more embodiments, be mixed and matched and substituted with other embodiments of guiding element 40 contained herein. In one or more embodiments, force may be applied symmetrically on vial 70 to center vial 70 over needle 30. In one or more embodiments, the guiding element barrels 44 illustrated in FIGS. 28A-35B may guide needle 30 into substantially the center of vial 70 and secure or otherwise engage vial 70 while a user draws medication from it. In one or more embodiments, force may be applied asymmetrically on vial 70 such that vial 70 is offset and applied against a portion of the inner wall of guiding element barrel 44. In one or more embodiments, the guiding element shaft 42 of guiding elements 40 illustrated in FIGS. 28A-35B may house and protect needle 30 and other devices. In one or more embodiments, once the medication has been extracted, the guiding elements 40 illustrated in FIGS. 28A-35B may be removed from medication delivery device 10, expose needle 30 and the medication may be administered to the patient.

Figure 27A:
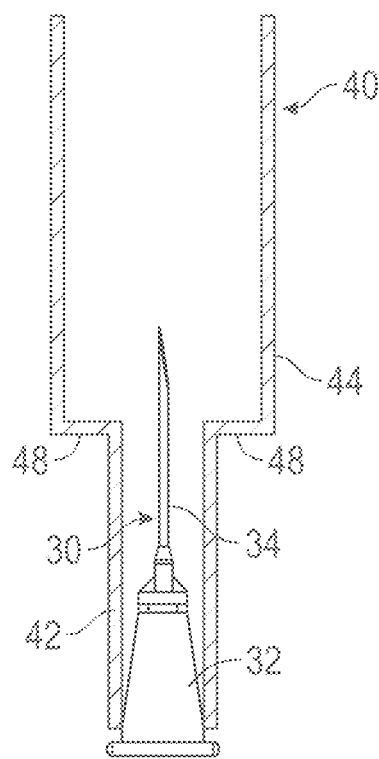
FIG. 27A shows a side view of one embodiment of a needle and a cross sectional view of one embodiment of guiding element which may include a transition section.

FIG. 27A shows a side view of one embodiment of needle 30 and a cross sectional view of one embodiment of guiding element 40 which may include a transition section 48 between guiding element shaft 42 and guiding element barrel 44. In one or more embodiments, transition section 48 may form a substantially right angle designed to engage cap 71 of vial 70 and control the depth needle 30 may access vial 70. In one or more embodiments, transition section 48 may aid in stabilizing the position of vial 70 while it is secured by guiding element barrel 44. In one or more embodiment, the embodiment of guiding element 40 illustrated in FIG. 27A may be used in conjunction with a medication delivery device 10 capable of automatically engaging volume limiter 50 for limiting the amount of medication that can be drawn from vial 70. As indicated above, in one or more embodiments, guiding element barrel 44 may guide needle 30 into substantially the center of vial 70 and secure or otherwise engage vial 70 while a user draws medication from it. As indicated above, in one or more embodiments, guiding element shaft 42 may house and protect needle 30 and others. As indicated above, in one or more embodiments, once the medication has been extracted, guiding element 40 may be removed from medication delivery device 10, expose needle 30 and the medication may be administered to the patient.

Figure 27B:
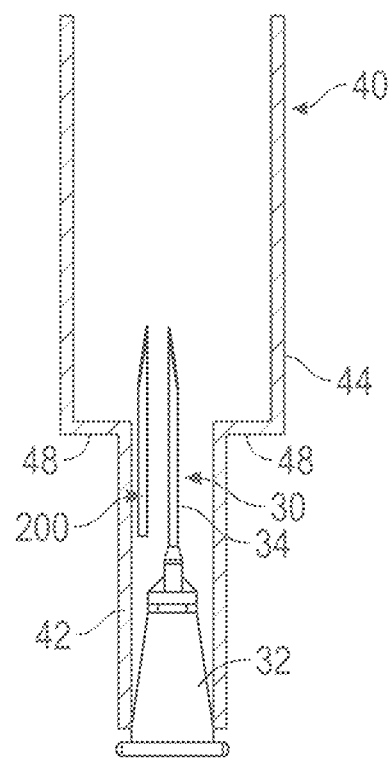
FIG. 27B shows a side view of the embodiment of the needle and a cross sectional view of the embodiment of the guiding element illustrated in FIG. 27A, albeit including a venting needle.

FIG. 27B shows a side view of the embodiment of needle 30 and a cross sectional view of the embodiment of guiding element 40 illustrated in FIG. 27A, albeit including a venting needle 200 which, in one or more embodiments, may puncture cap 71 of vial 70 and allow air ingress to vial 70 as medication may be withdrawn from vial 70 in order to prevent formation of a vacuum that may inhibit flow into syringe 20. In one or more embodiment, venting needle 200 may eliminate or reduce the need to force air into vial 70 to prevent a vacuum. In one or more embodiment, the embodiment of guiding element 40 illustrated in FIG. 27B may be used in conjunction with a medication delivery device 10 wherein the volume limber 50 is manually engaged for limiting the amount of medication that can be drawn from vial 70.

FIGS. 28A-33 show various embodiments of guiding element 40 designed with a means to accommodate different sized vials 70. In one or more embodiments, guiding element 40 may be configured with inserts, stepped walls, a spring-loaded interior sleeve and/or expanding walls or other materials to accommodate the foil range of vial sizes.

Figure 28A:
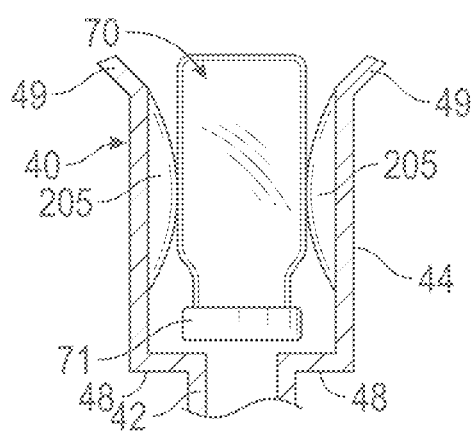
FIG. 28A shows a cross sectional view of one embodiment of a guiding element including at least two bow members.

FIG. 28A shows a cross sectional view of one embodiment of guiding element 40 including at least two bow members 205 for engaging and securing vial 70 when vial 70 is inserted into guiding element barrel 44. In one or more embodiments, the at least two bow members 205 may flex towards guiding element barrel 44 or otherwise move as vial 70 is inserted into guiding element barrel 44. In one or more embodiments, the at least two bow members 205 may flex towards guiding element barrel 44 at increasingly acute angles the larger the size of vials 70 that may be inserted in guiding element barrel 44. In one or more embodiments, the at least two bow members 205 may apply such force to vial 70 as necessary to secure vial 70 in guiding element barrel 44. Although not shown in FIG. 28A, in one or more embodiments, vial 70 may be removed from guiding element barrel 44 as desired by a user. As shown in FIG. 28A, guiding element barrel 44 may include transition section 48 between guiding element shaft 42 and guiding element barrel 44 which may form a substantially right angle designed to engage cap 71 of vial 70 and control the depth needle 30 may access vial 70 and aid in the stabilizing vial 70 while it is secured in guiding element barrel 44. In one or more embodiments, as shown in FIG. 28A, guiding element barrel 44 may include angled edges 49 for guiding vial 70 into guiding element barrel 44.

Figure 28B:
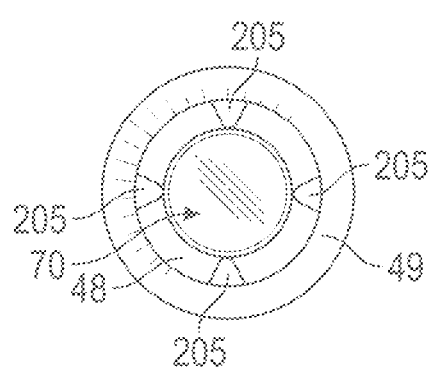
FIG. 28B shows a top view of the embodiment of the guiding element illustrated in FIG. 28A.

FIG. 28B shows a top view of the embodiment of guiding element 40 illustrated in FIG. 28A configured with four of the at least two bow members 205. Although not shown in FIG. 28A or 28B, in one or more embodiments, the at least two bow members 205 may assume a "Y" formation which provide four points of contact with vial 70. Although not shown in FIG. 28A or 28B, in one or more embodiments, guiding element 40 may include a single bow member 205 for engaging and securing vial 70 when vial 70 is inserted into guiding element barrel 44. In such a configuration, the single bow member 205 may engage vial 70 such that vial 70 is offset.

Figure 29A:
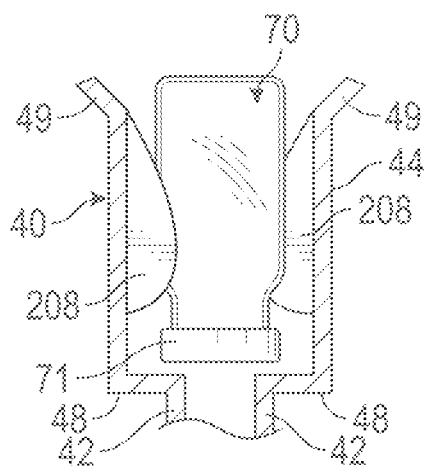
FIG. 29A shows a cross sectional view of one embodiment of a guiding element including at least three fins.

FIG. 29A shows a cross sectional view of one embodiment of guiding element 40 including at least three fins 208 (only two fins 208 are shown in FIG. 29A) for engaging and securing vial 70 when vial 70 is inserted into guiding element barrel 44. As shown in FIG. 29A, the at least three fins 208 may flex, pivot or articulate towards guiding element barrel 44 or otherwise move as vial 70 is inserted into guiding element barrel 44. In one or more embodiments, the at least three fins 208 may flex towards guiding element barrel 44 at increasingly acute angles the larger the size of vials 70 that may be inserted in guiding element barrel 44. In one or more embodiments, the at least three fins 208 may apply such force to vial 70 as necessary to secure vial 70 in guiding element barrel 44. Although not shown in FIG. 29A, in one or more embodiments, vial 70 may be removed from guiding element barrel 44 as desired by a user. As shown in FIG. 29A, guiding element barrel 44 may include transition section 48 between guiding element shaft 42 and guiding element barrel 44 which may form a substantially right angle designed to engage cap 71 of vial 70 and control the depth needle 30 may access vial 70 and aid in stabilizing vial 70 while it is secured in the guiding element barrel 44. In one or more embodiments, as shown in FIG. 29A, guiding element barrel 44 may include angled edges 49 for guiding vial 70 into guiding element barrel 44.

Figure 29B:
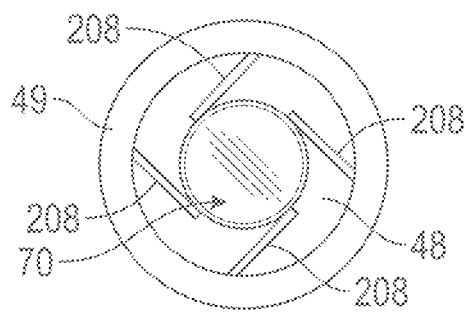
FIG. 29B shows a top view of the embodiment of the guiding element illustrated in FIG. 29A.

FIG. 29B shows a top view of the embodiment of guiding element 40 illustrated in FIG. 29A.

Figure 30A:
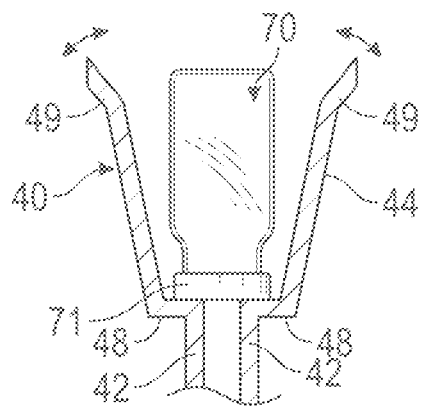
FIG. 30A shows a cross sectional view of one embodiment of a guiding element including a guiding element barrel with independently movable sections of the wall of said guiding element barrel.

FIG. 30A shows a cross sectional view of one embodiment of guiding element 40 including guiding element barrel 44 with independently movable sections of the wall of said guiding element barrel 44. Although not shown in FIG. 30A, the independently movable sections of the wall of guiding element barrel 44 may be designed to automatically adjust to the contour of vial 70 and engage and secure vial 70 when vial 70 is inserted into guiding element barrel 44. As shown in FIG. 30A, a space 209 may be located between each independently movable sections of the wall of said guiding element barrel 44.

Figure 30B:
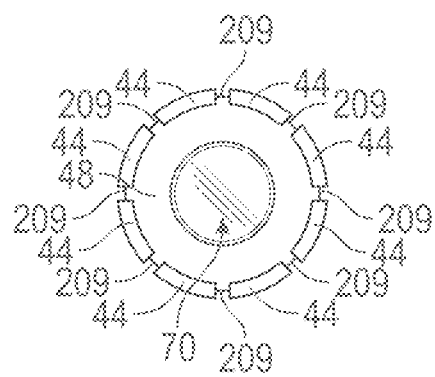
FIG. 30B shows a top view of the embodiment of the guiding element illustrated in FIG. 30A.

FIG. 30B shows atop view of the embodiment of guiding element 40 illustrated in FIG. 30A.

Figure 31A:
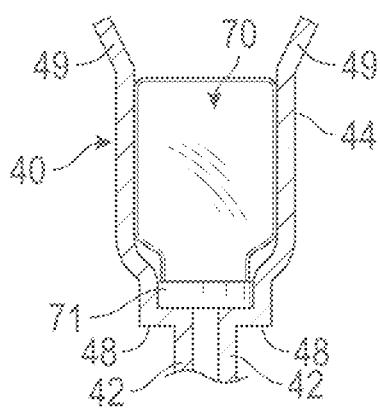
FIG. 31A shows a cross sectional view of one embodiment of a guiding element including a guiding element barrel, at least a portion of which may be designed with flexible or semi-flexible material.

FIG. 31A shows a cross sectional view of one embodiment of guiding element 40 including guiding element barrel 44, at least a portion of which may be designed with flexible or semi-flexible material that may automatically adjust to the contour of vial 70 and engage and secure vial 70 when vial 70 is inserted into guiding element barrel 44.

Figure 31B:
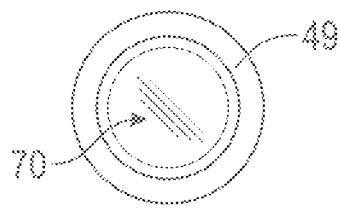
FIG. 31B shows a top view of the embodiment of the guiding element illustrated in FIG. 31A.

FIG. 31B shows a top view of the embodiment of guiding element 40 illustrated in FIG. 31A.

Figure 32A:
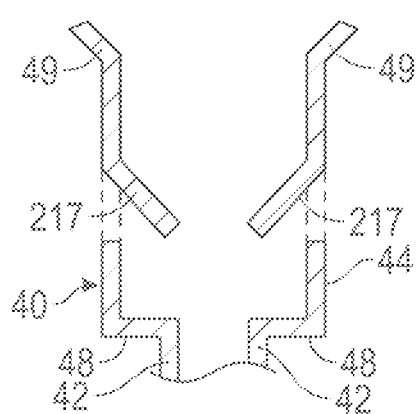
FIG. 32A shows a cross sectional view of one embodiment of a guiding element including at least one flexible member.

FIG. 32A shows a cross sectional view of one embodiment of guiding element 40 including at least one flexible member 217 for engaging and securing vial 70 when vial 70 is inserted into guiding element barrel 44. In one or more embodiments, the at least one flexible member 217 may flex towards guiding element barrel 44 or otherwise move as vial 70 is inserted into guiding element barrel 44 and then once cap 71 passes the end of the at least one flexible member 217 said at least one flexible member 217 may apply such force to vial 70 as necessary to secure vial 70 in guiding element barrel 44. In one or more embodiments, the embodiment of guiding element barrel 44 as illustrated in FIG. 32A may be designed to permanently retain vial 70 once it is placed in guiding element barrel 44.

Figure 32B:
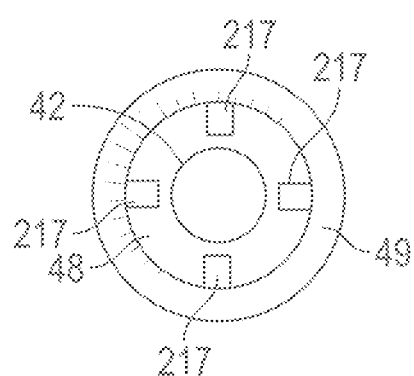
FIG. 32B shows a top view of the embodiment of the guiding element illustrated in FIG. 32A.

FIG. 32B shows a top view of the embodiment of guiding element 40 illustrated in FIG. 32A.

Figure 33:
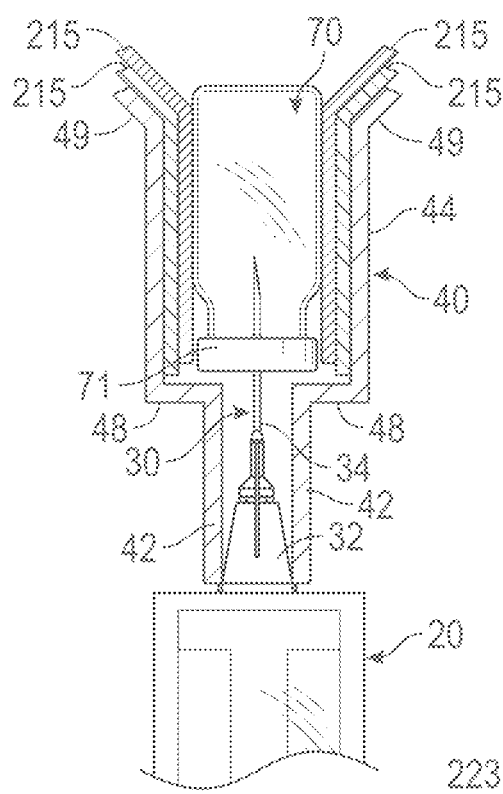
FIG. 33 shows a cross sectional view of one embodiment of a guiding element with at least one insert.

FIG. 33 shows a cross sectional view of one embodiment of guiding element 40 with at least one Insert 215 placed between guiding element barrel 44 and vial 70 in order to aid in the engagement, securement and stabilization of vial 70 when vial 70 is inserted into guiding element barrel 44. In one or more embodiments, the at least one insert 215 may be made from various materials, including rubber, plastic or other materials.

FIGS. 34A-35B show various embodiments of guiding element 40 assuming a cannula like configuration.

Figure 34A:
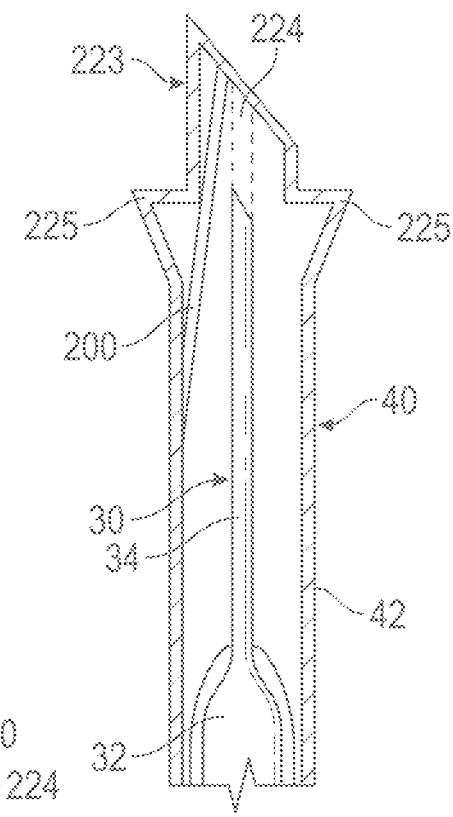
FIG. 34A shows a cross sectional view of one embodiment of a guiding element including a guiding element shaft configured like a semi-sharp cannula.

FIG. 34A shows a cross sectional view of one embodiment of guiding element 40 including guiding element shaft 42 configured like a semi-sharp cannula including a neck 223 designed to be sharp enough to puncture the rubber septum of vial 70 but not sharp enough to penetrate skin and a duct 224 where medication may flow from vial 70 to needle 30. Such configuration may provide a safe compact unit which may not require extensive fine motor control. As shown in FIG. 34A, in one or more embodiments, the cannula-like designed guiding element shaft 42 may house or enclose needle 30. Such configuration may prevent needle sticks and avoid having to adapt the disclosure to accommodate different sized vials 70 as one size cannula-like designed guiding element shaft 42 may fit various sized vials 70. In one or more embodiments, after the cannula-like designed guiding element shaft 42 is inserted into vial 70, medication from vial 70 may flow through duct 224, into and through needle 30 and into syringe 20. In one or more embodiments, after the cannula-like configured guiding element shaft 42 may be used to draw medication from vial 70, a user may remove cannula-like configured guiding element shaft 42, thereby exposing the pre-assembled needle 30 and perform the injection. Such configuration may avoid the disadvantages of using available cannula systems which required switching out the cannula after it is used to draw medication and then replacing it with a needle for injecting a patient. As indicated, in one or more embodiments, the cannula-like designed guiding element shaft 42 may only require removing the guiding element shaft 42 to expose an already attached needle 30, thus, in comparison to available cannulas, the disclosure reduces both the time and the number steps it takes for the procedure and the chance of dropping or otherwise contaminating or damaging needle 30 or others. Although not shown in FIG. 34A, the cannula-like designed guiding element shaft 42 may include safety shield 60 for covering needle 30 after use. As shown in FIG. 34A, the cannula-like designed guiding element shaft 42 may house more than one needle, such as venting needle 200 and needle 30. In one or more embodiments, venting needle 200 may allow air ingress into vial 70 as medication may be withdrawn from vial 70 in order to prevent the formation of a vacuum that may inhibit flow into syringe 20. Although not shown in FIG. 34A, in one or more embodiments, the cannula-like designed guiding element shaft 42 may only include a single needle 30. In one or more embodiments, the cannula-like designed guiding element shaft 42 may be configured to engage cap 71 or another aspect of vial 70 in such a way so as to prevent guiding element 40 from traveling into vial 70 beyond a certain point. For example, as shown in FIG. 34A, end 225 of the cannula-like designed guiding element shaft 42 may be flared to prevent overtravel into vial 70.

Figure 34B:
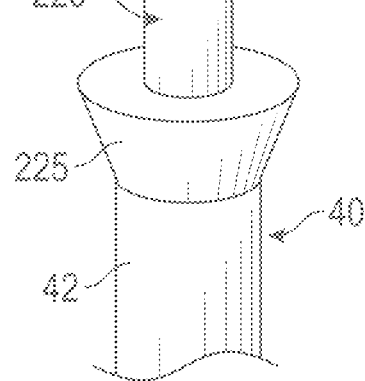
FIG. 34B shows a perspective view of the embodiment of the guiding element illustrated in FIG. 34A and including a venting needle.

FIG. 34B shows a perspective view of the embodiment of guiding element 40 illustrated in FIG. 34A.

FIG. 35A shows a cross sectional view of the embodiment of guiding element 40 illustrated in FIG. 34A, albeit neck 223 assumes a cone configuration, duct 224 assumes a "Y" configuration allowing two pathways for medication to flow from vial 70 into needle 30 and only a single needle 30 is present (i.e. no venting needle 200 is illustrated).

FIG. 35B shows a perspective view of the embodiment of guiding element 40 illustrated in FIG. 35A.

FIG. 36 shows a perspective view of one embodiment of medication delivery device 10 in a blister package 301 (or simply package 301) with a blister lid 305 being peeled open. Although not shown in FIG. 36, in one or more embodiments, vial 70 of medication may be sold or otherwise provided in package 301 with medication delivery device 10. In one or more embodiments, vial 70 of medication may be sold or otherwise provided separate from package 301 allowing users to replace the medication without being required to also replace medication delivery device 10. In one or more embodiments, the expiration date of medication delivery device 10 may not be dependent upon the expiration date of the medication that is to be administered to patients. In one or more embodiments, a patient may be able to replace outdated medication without having to replace medication delivery device 10, thereby allowing users to keep quality medication on hand without having to incur additional expense of replacing medication delivery device 10.

Figure 37:
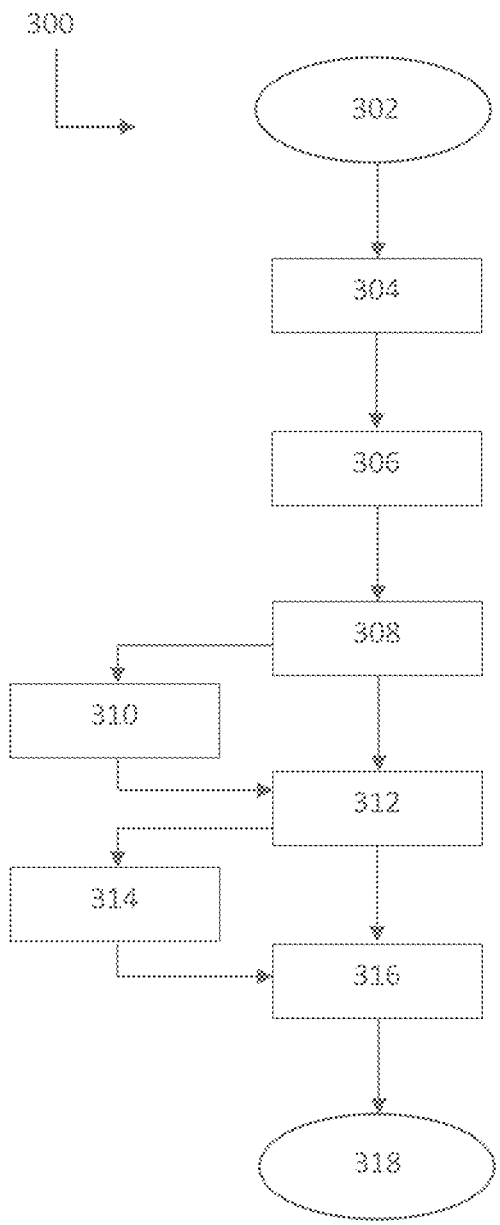
FIG. 37 is a flow diagram that depicts one embodiment of a method for using a medication delivery device in accordance with one embodiment.

FIG. 37 is a flow diagram that depicts one embodiment of a method 300 for using medication delivery device 10 in accordance with one embodiment. The method 300 for using medication delivery device 10 as illustrated in flow diagram FIG. 37 may be customized, flexible and adapted to various circumstances and situations. Method 300 may be used to administer medication to patients. In step 302, a user enters the process. In one or more embodiments, the user may open package 301 and remove medication delivery device 10. A user may hold medication delivery device 10 in an upright position such that guiding element 40 is pointed up. In one or more embodiments, the user may remove a safety cap from needle 30 if present. In step 304, a user may insert vial 70 into guiding element barrel 44 of guiding element 40 such that needle 30 accesses vial 70 below the medication level. In step 306, a user may draw back on plunger 25 to fill syringe 20 with medication until volume limiter 50 engages the plunger 25 and prevents it from traveling further back (such as when second end 28 of engagement section 26 engages bottom surface 53 of volume limiter 50). In one or more embodiments, plunger 25 may be sold or otherwise provided already depressed into the syringe barrel 22 such that a user may draw back on it as described in step 306. In one or more embodiments, the user may verify dose. In step 308, a user may remove guiding element 40 and vial 70 from needle 30 to expose needle 30. In one or more embodiments, a user may need to expel excess air from syringe 20 after removing vial 70. In step 310, a user may optionally disengage volume limiter 50 (such as by manually rotating plunger 25 such that the engagement section 26 of plunger 25 is no longer in contact with the first surface 57 of opening 52 and/or such as by shifting the volume limiter 50 into an alternative position which disengages opening 52 from the engagement section 26 of the plunger 25). In step 312, a user may insert needle 30 into a patient. In step 314, a user may optionally draw back plunger 25 to check for placement, flash or for other purposes. In step 316, a user may depress plunger 25 to inject the medication into the patient. In step 318, a user may withdraw medication delivery device 10 from the patient and end the process.

Figure 38:
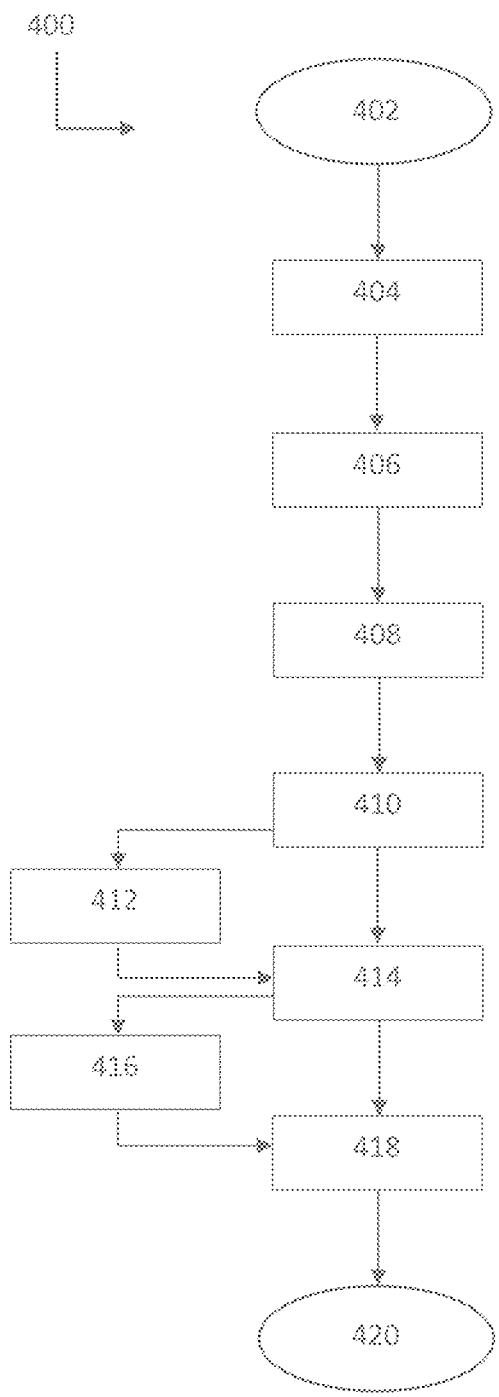
FIG. 38 is a flow diagram that depicts one embodiment of another method for using a medication delivery device in accordance with one embodiment.

FIG. 38 is a flow diagram that depicts one embodiment of a method 400 for using medication delivery device 10 in accordance with one embodiment. The method 400 for using medication delivery device 10 as illustrated in flow diagram FIG. 38 may be customized, flexible and adapted to various circumstances and situations. Method 400 may be used to administer medication to patients. In step 402, a user enters the process. In one or more embodiments, the user may open package 301 and remove medication delivery device 10. A user may hold medication delivery device 10 in an upright position such that guiding element 40 is pointed up. In one or more embodiments, the user may remove a safety cap from needle 30 if present. In step 404, a user may insert vial 70 into guiding element barrel 44 of guiding element 40 such that needle 30 accesses vial 70 below the medication level. In step 406, a user may depress plunger 25 to force air into vial 70. In one or more embodiments, the user may depress plunger 25 to engage volume limiter 50. In one or more embodiments, the user may depress plunger 25 either until the plunger stopper 29 engages the bottom of syringe barrel 22 or until volume limiter 50 prevents the further travel of plunger 25 (such as when first end 27 of engagement section 26 engages top surface 51 of volume limiter 50). In one or more embodiments, plunger 25 may be sold or otherwise provided already inserted through opening 52 of volume limiter 50 but not yet depressed into the syringe barrel 22. In one or more embodiments, although plunger 25 may come already inserted through opening 52 of volume limiter 50, volume limiter 50 may not be fully engaged until plunger 25 is depressed as described in step 406. In one or more embodiments, the user may verify dose. In one or more embodiments, a pressurized vial 70 may fill syringe 20 until plunger 25 is stopped by volume limiter 50. In step 408, a user may allow plunger 25 to automatically draw back and syringe 20 to fill with the medication until volume limiter 50 prevents further travel of plunger 25 (such when second end 28 of engagement section 26 engages bottom surface 53 of volume limiter 50). In step 410, a user may remove guiding element 40 and vial 70 from needle 30 to expose needle 30. In one or more embodiments, a user may need to expel excess air from syringe 20 after removing vial 70. In step 412, a user may optionally disengage volume limiter 50 (such as by manually rotating plunger 25 such that the engagement section 26 of plunger 25 is no longer in contact with the first surface 57 of opening 52 and/or such as by shifting the volume limiter 50 into an alternative position which disengages opening 52 from the engagement section 26 of the plunger 25). In step 414, a user may insert needle 30 into a patient. In step 416, a user may optionally draw back plunger 25 to check for placement, flash or for other purposes. In step 418, a user may depress plunger 25 to inject the medication into the patient. In step 420, a user may withdraw medication delivery device 10 from the patient and end the process.

Different embodiments of the disclosure may implement the above scenario(s) and/or variations of the above scenario(s). In one or more embodiment, any of the structures, functions, and/or features of any aspect of the disclosure expressly and/or inherently described and/or illustrated herein may be combined with any of the structures, functions, and/or features of any other aspect of the disclosure expressly and/or Inherently described and/or illustrated herein. In one or more embodiments, each component of the disclosures may be provided in any color.

In one or more embodiments, other modifications may be made to the embodiments illustrated in the drawings and/or otherwise disclosed herein, which may include and/or have the capacity to utilize abilities, systems, devices, articles, means, functionality, features, methods and/or uses expressly, not expressly and/or impliedly described herein and/or illustrated in the drawings to this application but which may be obvious to one skilled in the art, whether developed later or known at the time of filing.

It should be understood that the present systems, devices, means, methods and structures are not intended to be limited to the particular forms disclosed; rather, they are to cover all combinations, modifications, equivalents and alternatives. A system, device, article, means, method or structure that is configured in a certain way may be configured in at least that way, but may also be configured in ways that are not described or illustrated. The disclosure may be configured to function with a variety of systems, devices, means, methods, and structures. Different materials may be used for individual components. Different materials may be combined in a single component.

The present disclosure may be embodied in other specific forms without departing from its spirit or essential characteristics. It is appreciated that various features of the above described examples and embodiments may be mixed and matched to form a variety of other combinations and alternatives. It is also appreciated that devices, methods and systems disclosed herein should not be limited simply to methods, systems and devices for administering medication. The described embodiments are to be considered in all respects as illustrative and not restrictive. Other embodiments and/or implementations are within the scope of the following claims and at least all changes which come within the meaning and range of equivalency of the claims are to be embraced within their scope. The scope of the disclosure may be indicated by the appended claims rather than by any of the foregoing description.

What is claimed is:

1. A medication delivery device, comprising:
 a syringe, comprising: a flange, a syringe barrel, and a plunger slideably disposed in the syringe barrel, wherein the plunger comprises an engagement section, wherein the engagement section is recessed into the plunger and comprises: a first end and an engagement surface;
 a needle;
 a safety sleeve;
 a guiding element, comprising: a guiding element shaft that houses a portion of the needle and a guiding element barrel that receives and engages a vial;
 a volume limiter operably connected to the flange of the syringe, wherein the volume limiter comprises: a top surface, a bottom surface, and an opening through which the plunger is configured to travel, wherein the opening of the volume limiter comprises a first surface;
 a retention member operably connected to the volume limiter, wherein the retention member applies force to the volume limiter such that the volume limiter resiliently engages the plunger; and
 wherein, when the plunger and the volume limiter engage each other, the bottom surface of the volume limiter restricts the longitudinal distance that the plunger can be drawn and thereby limits the amount of medication that can be drawn from the vial.

2. The medication delivery device of claim 1, wherein the retention member is secured around a surface of the syringe and an oppositely situated surface of the volume limiter.

3. The medication delivery device of claim 1,
 wherein the vial comprises a cap and an exterior side wall; and
 wherein the length of the guiding element barrel is such that it extends beyond the cap of the vial to engage the exterior side wall when the vial has been inserted into the guiding element barrel.

4. The medication delivery device of claim 1, wherein the bottom surface of the volume limiter restricts the longitudinal distance that the plunger can be drawn by engaging the first end of the engagement section.

5. The medication delivery device of claim 1, wherein the volume limiter further comprises:
 a first bottom ledge and a second bottom ledge located on the bottom surface of the volume limiter, wherein the first bottom ledge and the second bottom ledge are arranged to allow the flange of the syringe to transition in between them; and
 a first flange housing element that receives and secures the flange.

6. The medication delivery device of claim 4,
 wherein the engagement surface of the plunger and the first surface of the volume limiter's opening are configured to engage each other, and wherein the plunger is twistable such that when the engagement surface and the first surface engage each other and the plunger is twisted, the engagement surface rotates away from the first surface and the first end of the engagement section disengages from the bottom surface of the volume limiter, thereby allowing the plunger to be drawn without being restricted by the bottom surface.

7. The medication delivery device of claim 1, wherein the volume limiter is resiliently shiftable on the flange of the syringe.

8. The medication delivery device of claim 1, wherein the syringe further comprises a syringe tip and the needle comprises a needle hub, wherein one end of the safety sleeve is operably connected to the needle hub and another end of the safety sleeve is operably connected to the syringe tip.

9. The medication delivery device of claim 1, wherein, when the plunger is depressed through the opening of the volume limiter such that the first surface of the opening passes over the first end of the engagement section, the retention member causes the volume limiter to transition on the flange such that the first surface automatically engages the engagement surface.

10. The medication delivery device of claim 1, further comprising a venting needle that is configured to allow air into the vial when medication is drawn from the vial.

11. The medication delivery device of claim 1, wherein the guiding element further comprises at least one flexible member that engages and secures the vial when the vial is inserted into the guiding element barrel.

12. The medication delivery device of claim 1, wherein the guiding element barrel receives and engages the vial such that the needle is placed into substantially the center of a cap of the vial when the vial is inserted into the guiding element barrel.

13. The medication delivery device of claim 1, further comprising a means for engaging vials of more than one size.

14. The medication delivery device of claim 1, wherein the guiding element barrel comprises at least two bow members that engage and secure the vial when the vial is inserted into guiding element barrel.

15. The medication delivery device of claim 1, wherein the guiding element barrel comprises at least three fins that engage and secure the vial when the vial is inserted into guiding element barrel.

16. The medication delivery device of claim 1, wherein at least a portion of the guiding element barrel is made of material that automatically adjusts to the contour of the vial when the vial is inserted into guiding element barrel.

17. The medication deliver device of claim 1,
wherein the engagement section of the plunger further comprises a second end;
wherein the length of the engagement surface of the engagement section is defined by the distance between the first end and the second end; and
wherein, when the plunger and the volume limiter engage each other, the top surface of the volume limiter restricts the longitudinal distance that the plunger can be depressed.

18. The medication delivery device of claim 1, wherein the retention member applies force to the volume limiter such that the first surface of the volume limiter's opening resiliently engages the engagement surface of the plunger's engagement section.

19. A method for administering medication using a medication delivery device,
the medication delivery device, comprising:
a syringe, comprising: a flange, a syringe barrel, and a plunger slideably disposed in the syringe barrel, wherein the plunger comprises an engagement section, wherein the engagement section is recessed into the plunger and comprises: a first end and an engagement surface;
a needle;
a safety sleeve;
a guiding element, comprising: a guiding element shaft that houses a portion of the needle and a guiding element barrel that receives and engages a vial;
a volume limiter operably connected to the flange of the syringe, wherein the volume limiter comprises: a top surface, a bottom surface, and an opening through which the plunger is configured to travel, wherein the opening of the volume limiter comprises a first surface;
a retention member operably connected to the volume limiter, wherein the retention member applies force to the volume limiter such that the volume limiter resiliently engages the plunger; and
wherein, when the plunger and the volume limiter engage each other, the bottom surface of the volume limiter restricts the longitudinal distance that the plunger can be drawn and thereby limits the amount of medication that can be drawn from the vial;
the method for administering medication using the medication delivery device, comprising:
inserting the vial into the guiding element barrel such that the needle accesses the vial below a medication level;
drawing back on the plunger to fill the syringe with medication until the volume limiter prevents further travel of the plunger;
removing the guiding element and the vial from the needle to expose the needle;
inserting the needle into the patient;
depressing the plunger to inject the medication into the patient; and
withdrawing the medication delivery device from the patient.

20. A method for administering medication using a medication delivery device,
the medication delivery device, comprising:
a syringe, comprising: a flange, a syringe barrel, and a plunger slideably disposed in the syringe barrel, wherein the plunger comprises an engagement section, wherein the engagement section is recessed into the plunger and comprises: a first end and an engagement surface;
a needle;
a safety sleeve;
a guiding element, comprising: a guiding element shaft that houses a portion of the needle and a guiding element barrel that receives and engages a vial;
a volume limiter operably connected to the flange of the syringe, wherein the volume limiter comprises: a top surface, a bottom surface, and an opening through which the plunger is configured to travel, wherein the opening of the volume limiter comprises a first surface;
a retention member operably connected to the volume limiter, wherein the retention member applies force to the volume limiter such that the volume limiter resiliently engages the plunger; and
wherein, when the plunger and the volume limiter engage each other, the bottom surface of the volume limiter restricts the longitudinal distance that the plunger can be drawn and thereby limits the amount of medication that can be drawn from the vial;
the method for administering medication using the medication delivery device, comprising:
inserting the vial into the guiding element barrel such that the needle accesses the vial below a medication level;
depressing the plunger to force air into the vial;
allowing the plunger to automatically draw back to fill the syringe with medication until the volume limiter prevents further travel of the plunger;
removing the guiding element and the vial from the needle to expose the needle;
inserting the needle into the patient;
depressing the plunger to inject the medication into the patient; and
withdrawing the medication delivery device from the patient.

* * * * *